(12) United States Patent
Barak et al.

(10) Patent No.: US 11,406,273 B2
(45) Date of Patent: Aug. 9, 2022

(54) CONTINUOUS BLOOD PRESSURE MEASUREMENT

(71) Applicant: SENSIFREE LTD., Petach Tikva (IL)

(72) Inventors: Ilan Barak, Kfar Saba (IL); Eran Agmon, Sunnyvale, CA (US); Roi Klein, Kiryat Bialik (IL); Nadav Neuberger, Wachtberg (DE); Alexei Nomazov, Ramla (IL)

(73) Assignee: Sensifree Ltd., Kfar Saba (IL)

( * ) Notice: Subject to any disclaimer, the term of this patent is extended or adjusted under 35 U.S.C. 154(b) by 171 days.

(21) Appl. No.: 16/758,012

(22) PCT Filed: Dec. 22, 2018

(86) PCT No.: PCT/US2018/067412
§ 371 (c)(1),
(2) Date: Apr. 21, 2020

(87) PCT Pub. No.: WO2019/126813
PCT Pub. Date: Jun. 27, 2019

(65) Prior Publication Data
US 2020/0315471 A1    Oct. 8, 2020

Related U.S. Application Data

(60) Provisional application No. 62/609,435, filed on Dec. 22, 2017.

(51) Int. Cl.
*A61B 5/022*     (2006.01)
*A61B 5/00*      (2006.01)
(Continued)

(52) U.S. Cl.
CPC ........ *A61B 5/02225* (2013.01); *A61B 5/0004* (2013.01); *A61B 5/021* (2013.01);
(Continued)

(58) Field of Classification Search
CPC ....... A61B 5/021; A61B 5/029; A61B 5/0205; A61B 5/14551; A61B 5/02028;
(Continued)

(56) References Cited

U.S. PATENT DOCUMENTS 5,101,828 A * 4/1992 Welkowitz ............. A61B 5/021
                                                        600/481
5,211,177 A * 5/1993 Chesney ............ A61B 5/02007
                                                        600/481

(Continued)

FOREIGN PATENT DOCUMENTS

WO    WO2019/126813 A1    6/2019

OTHER PUBLICATIONS

Abdi, M., Karimi, A., Navidbakhsh, M., Pirzad Jahromi, G., & Hassani, K. A lumped parameter mathematical model to analyze the effects of tachycardia and bradycardia on the cardiovascular system. International Journal of Numerical Modelling: Electronic Networks, Devices and Fields, 28(3), 346-35 (Year: 2015).*

(Continued)

*Primary Examiner* — Daniel L Cerioni
*Assistant Examiner* — Jonathan E. Cooper
(74) *Attorney, Agent, or Firm* — Neifeld IP Law

(57) ABSTRACT

We disclose a system and method for estimating values of hemodynamic parameters of a subject, by calibrating arterial pressure during one time and tracking arterial pressure at another time.

18 Claims, 11 Drawing Sheets

(51) Int. Cl.
 *A61B 5/02* (2006.01)
 *A61B 5/021* (2006.01)
 *A61B 5/024* (2006.01)
 *G16H 50/50* (2018.01)

(52) U.S. Cl.
 CPC ...... *A61B 5/02028* (2013.01); *A61B 5/02427* (2013.01); *A61B 5/02444* (2013.01); *A61B 5/6824* (2013.01); *A61B 5/6826* (2013.01); *A61B 5/6843* (2013.01); *A61B 5/72* (2013.01); *A61B 5/7225* (2013.01); *A61B 5/7235* (2013.01); *A61B 5/7257* (2013.01); *A61B 5/742* (2013.01); *A61B 5/743* (2013.01); *G16H 50/50* (2018.01); *A61B 2560/0223* (2013.01)

(58) Field of Classification Search
 CPC ... A61B 5/02225; A61B 5/02108; A61B 5/02; A61B 5/022
 See application file for complete search history.

(56) References Cited

U.S. PATENT DOCUMENTS

| | | |
|---|---|---|
| 5,579,776 A | 12/1996 | Medero |
| 5,928,155 A | 7/1999 | Eggers |
| 6,413,223 B1 | 7/2002 | Yang |
| 9,107,588 B2 | 8/2015 | Katayama |
| 10,667,701 B1* | 6/2020 | Adithya ................ A61B 5/021 600/481 |
| 2002/0055680 A1 | 5/2002 | Miele |
| 2003/0135124 A1 | 7/2003 | Russell |
| 2005/0124903 A1* | 6/2005 | Roteliuk ................ A61B 5/029 600/526 |
| 2007/0016028 A1 | 1/2007 | Donaldson |
| 2009/0105556 A1* | 4/2009 | Fricke ................ A61B 5/0205 600/301 |
| 2009/0281399 A1 | 11/2009 | Keel |
| 2010/0081945 A1* | 4/2010 | Sethi ................ A61B 5/029 600/481 |
| 2010/0204592 A1 | 8/2010 | Hatib |
| 2011/0237962 A1 | 9/2011 | Hersh |
| 2012/0123246 A1 | 5/2012 | King |
| 2015/0112211 A1 | 4/2015 | Purdy |
| 2015/0164339 A1 | 6/2015 | Xu |
| 2016/0206804 A1 | 7/2016 | Holmer |
| 2017/0224232 A1* | 8/2017 | Maarek ................ A61B 5/02416 |
| 2017/0346457 A1 | 11/2017 | Obata |
| 2019/0133534 A1 | 5/2019 | Hu |

OTHER PUBLICATIONS

International Search Report and Written Opinion in PCT1US201S/067412.

* cited by examiner

CONTINUOUS BLOOD PRESSURE MEASUREMENT

RELATED APPLICATIONS

U.S. provisional application 62/609,435 titled "Estimating the relationship between MAP value and pulse amplitude and methods to achieve so," is hereby incorporated herein by reference.

BACKGROUND

Field of the Invention

This invention relates to measurement of human blood pressure values (BPVs).

Sphygmomanometers, tonometers, and Penaz devices, for measuring blood pressure, are known. See for example U.S. Pat. No. 5,579,776 (cuff); U.S. Pat. No. 6,413,223 (tonometer); and U.S. Pat. No. 9,107,588 (Penaz device). Hemodynamic parameters include Mean Arterial Pressure (MAP), Pulse Pressure (PP), Systolic pressure (Ps), Diastolic pressure (Pd), and Stroke Volume Variation (SVV).

A medical practitioner normally uses a manual sphygmomanometer and a stethoscope to determine Ps and Pd. A convention formula for estimating MAP from Ps, and Pd is:

$$MAP = \tfrac{2}{3}Pd + \tfrac{1}{3}Ps. \tag{1}$$

Oscillometric cuff based sphygmomanometers may determine MAP, Ps, and Pd directly from pressure data without using this formula.

A cardiac cycle is the sequence of events that occurs when the heart beats. There are two phases of the cardiac cycle. In the diastole phase, the heart ventricles are relaxed and the heart fills with blood. In the systole phase, the ventricles contract and pump blood out of the heart and to arteries. Arterial pressure waves resulting from one cardiac cycle include a first segment associated with systole followed by a second phase associated with diastole. The second phase typically includes a dicrotic notch, so that the arterial pressure wave associated with each cardiac cycle has two maxima, one on either side of the dicrotic notch.

Definitions

Herein after "subject" means human or mammal.

Herein after, an "arterial pulse" means the signal associated with the pressure variation over time of one complete cardiac cycle.

Hereinafter, a "cardiac time period" means a time period corresponding to an individual arterial pulse. The cardiac time period is also referred to herein after as the InterBeat Interval, and as IBI.

Hereinafter, a processing system defines a system that can implement algorithms for processing signals obtained from biometric transducers.

A processing system comprises a processing unit and memory. The processing unit may be virtualized in which case it is stored as computer code in memory. Thus, both the processing unit and the memory are implemented using hardware. Hardware refers to physical components that alter electrical or optical signals, such as resistors, capacitors, inductors, diodes, transistors, light emitting diodes, and lasers. Preferably, a processing system comprises a digital processing system which processes digital data. Digital data refers to discrete or discontinuous representation of information. Preferably, both the processing unit and the memory of a digital processing system each comprise at least one digital electronic integrated circuit. Alternatively, a digital processing system may be implemented with photonic computing components. A processing unit could also comprises an analog processing unit. The processing unit of a processing system may comprises components that are remotely located from one another. Memory of a processing system may also comprise components that are remotely located form one another.

Hereinafter, "F( . . . )" means "a function of" the elements listed within the parenthesis. This does not mean the each recitation "F( . . . )" refers to the same function.

Hereinafter, SV is an acronym for Stroke Volume. Stroke Volume means the volume of blood ejected from a ventricle of a heart of a subject during one cardiac cycle.

Hereinafter, a tracking sensor means any biometric transducer and a compatible front end capable of providing a signal comprising plural sampled values correlated to arterial pressure change of some region within the subject, during each cardiac cycle.

Hereinafter, when describing Fourier transform of a real valued signal, the description relates to the positive frequencies only.

Stroke Volume Variation, SVV, is a measure of variation in SV from two or more cardiac cycles.

A cardiovascular model is a model that relates blood flow (in volume per time) to blood pressure of a subject.

Electrical model means a model in the form of a mathematical description of an electrical equivalent circuit that represents the behavior of an electrical system.

SUMMARY OF THE INVENTION

We disclose blood pressure measurement systems and methods using a tracking transducer and tracking transducer front end, for tracking a subject's BPVs over an extended period of time. These blood pressure measurement systems and methods enable tracking BPVs for each arterial pulse. Preferably, the tracking transducer does not restrict blood flow and is not within the body. The tracking transducer provides a transduced signal to the tracking transducer front end. An output of the tracking transducer front end provides a signal that is correlated to arterial pressure in the region of the subject from which the tracking transducer obtains signal. Herein after, a tracking sensor refers to both the tracking transducer and the tracking transducer front end. The tracking sensor is capable of providing plural values correlating to arterial pressure during a single cardiac cycle. (For example, plural sampled values of a continuous signal at several times during a single cardiac cycle to provide plural values during a cardiac cycle.)

The transducer typically includes a plurality of LED's for generating light to transmit to a blood vessel to be measured, and a pin diode acting as an optical to electrical transducer converting the received light to an electrical signal. A front end circuit amplifies, filters and samples the signal from the tracking sensor transducer. The front end outputs a sequence of values corresponding to the value output from the tracking sensor transducer over time. The sampling frequency must be high enough so that the cardiac cycle can be distinguished. This sampling frequency must be at least 4 Hertz (Hz), preferably greater than 10 Hz, more preferably greater than 32 Hz. The sampling frequency is preferably less than 1 terahertz, and more preferably less than 10,000 Hz, and still more preferably less than 1,000 Hz. A practical upper limit to the sampling frequency is determined by the response time of the sensor, the duty cycle required to obtain a reasonable signal to noise ratio, and the upper frequency at which the sensor components respond. This limit may be about 10 GHz. If conductive cabling is used to carry the sensor signal to remote processing circuitry, signal dispersion in the cabling may result in a sampling frequency upper limit of 1 GHz.

The tracking sensor may comprise a PPG (photoplethysmography) transducer, reflective or transmissive, Electromagnetic wave sensor, RADAR sensor, a bioimpedance sensor, a pressure sensor like an applanation tonometer, or an ultrasonic sensor. The tracking sensor may be mounted, implanted, or positioned adjacent any location of the body of the subject where the output of the sensor correlates to arterial pressure These locations include but are not limited to the wrist, finger, arm, torso, leg, foot, head, forehead, earlobe, nose, and cheek.

In the preferred embodiment, the tracking sensor comprises a standard fingertip PPG transducer clipped or secured to a tip of a finger of the subject. PPG transducers are typically used for determining a subject's oxygen saturation level. Typically, PCMs (Patient Care Monitors) obtain signals from PPG sensors (for determining a subject's oxygen saturation level) at a sampling rate of between 100 and 200 Hz. Typical PPG sensors transduce signals at 660 nm and 940 nm, and combine the magnitude of both transduced signals within the sensor to provide a single sensor output signal. Embodiments use the signal received in a PCM from a PPG transducer as the tracking signal. For this reason, embodiments contemplate arterial pressure at 100 to 200 Hz. Embodiments employ a PCM, modified to perform the signal processing disclosed herein, for calibration and monitoring. These PCMs may also include a port for receiving data from one of the aforementioned types of calibration sensors. Disclosed methods comprise normalizing MAP, Ps, Pd arterial pressures data from the tracking sensor (tracking data), using values for MAP, Ps, and Pd, derived from a calibration sensor.

The calibration sensor is designed to provide signals from which a value for MAP and a value for PP (the difference between the Systolic pressure and the Diastolic pressure) for a subject can be determined. Sensors that provide such signals and can function as the aforementioned calibration sensor are well known, and include sphygmomanometers, tonometers, and Penaz devices. The calibration sensor may also comprise a pressure transducer inside an artery, or connected via a fluid filled tube to an artery.

Disclosed methods also comprise determining from the tracking data, time periods corresponding to individual cardiac cycles.

Disclosed methods comprise, performing a DFT on tracking data for a cardiac pulse.

Disclosed methods comprise replacing a DC value for the DFT spectrum of an arterial pulse obtained from a tracking sensor, with some nonzero value.

Disclosed methods comprise replacing a DC value for the DFT spectrum of an arterial pulse obtained from a tracking sensor, with values derived from the calibration sensor and the DFT of the tracking data.

Disclosed methods comprise determining from data provided by the tracking sensor, and a calibration, MAP, systolic (Ps), and Diastolic (Pd) pressures, on a pulse by pulse basis.

In a first aspect, we provide systems and methods for using the systems for estimating values of hemodynamic parameters of a subject, comprising: a processing system comprising a processing unit and memory; wherein the processing system is designed to receive calibration sensor data that relates to arterial pressure from a calibration sensor; wherein the processing system is designed to receive tracking sensor data from a tracking sensor; the processing system is designed to calculate estimated hemodynamic values of a hemodynamic parameter based upon: one or more outputs of a DFT of tracking sensor data relating to the arterial pressure, and which tracking sensor data was obtained from the subject during a calibration time period; at least two of MAP, PP, Ps, and Pd values from data obtained from the subject during the calibration time period; one or more outputs of a DFT of tracking sensor data relating to the arterial pressure, which tracking sensor data was obtained during a tracking time period; and wherein the tracking time period is different from the calibration time period; wherein the processing system is designed to display, store or transmit the estimated hemodynamic values.

Dependent features of this first aspect include: wherein the processing system is designed to calculate an FSUB value for an FSUB function; wherein FSUB is a function of variables comprising: MAP; PP; and a value of a harmonic of a DFT of tracking sensor data; and wherein the processing system is designed to determine parameters of a fitting function by fitting the fitting function to another function of output of a DFT of tracking sensor data, for data obtained from the subject during the calibration time period; and wherein a parameter of the fitting function depends upon MAP; and wherein the processing system is designed to determine parameters of a fitting function by fitting the fitting function to another function of output of a DFT of tracking sensor data, for data obtained from the subject during the tracking time period; and wherein the processing system is designed to hold constant the value of at least one determined parameter that was determined from data obtained from the subject during the calibration time period, when fitting tracking data during the tracking time period; and wherein the processing system is designed to calculate a value for MAP that relates to blood pressure of the subject during the tracking time period, from values for parameters calculated during the calibration time period, and tracking sensor data obtained from the subject during the tracking time period; and wherein the processing system is designed to calculate a value for MAP that relates to blood pressure of the subject during the tracking time period, from data also comprising the value for MAP obtained from the subject during the calibration time period; wherein the processing system is designed to determine a value for MAP by computations comprising computing the function.

MAPest=MAPcalib*$P(w0est)/Q(w0est)*Q(w0calib)/P(w0calib)$, where:

P represents a polynomial; Q represents a polynomial; w0est is a model parameter; w0Calib is a model parameter; and MAPcalib is a value for MAP obtained during a calibration time period; and wherein the processing system is designed to calculate a value for MAP by computations comprising computing the function MAPest=MAPcalib*$w0est2/w0calib2$, where: w0est is a model parameter; w0calib is a model parameter; and MAPcalib is a value for MAP obtained during a calibration time period; and wherein the processing system is designed to calculate a PP tracking value for PP from values for parameters determined during the calibration fitting and the tracking fitting, and the value for PP obtained during that calibration time period; and wherein the processing system is designed to determine a PP tracking value for PP from values for parameters determined during the calibration fitting and the tracking fitting, the value for PP obtained during that calibration time period, and the value of at least one arterial time period during the calibration time period and the value of at least one arterial time period during the tracking time period; and wherein system further comprises: a calibration sensor; a tracking sensor; and a device for visually displaying or transmitting values for hemodynamic parameters; and wherein the processing system is designed to compute values from (1) values of a DFT of tracking sensor data and (2) a value for FSUB calculated using MAP; PP; and a value of a harmonic of a DFT of that tracking sensor data; and wherein said processing system stores a combined electrical model that corresponds to a cardiovascular model; wherein said combined electrical model comprises a current source; a load; and at least one two-port network; and an equipotential potential connection between output of said current source and input of both said load and said at least one two-port network; and wherein said combined electrical model comprises a second two-port network that has an equipotential connection to an output of said least one two-port network; and wherein said processing system stores an electrical model that comprises a series connection of an inductor and capacitor, and capacitance of said capacitor is proportional to 1/MAP; and wherein said processing system stores an electrical model that comprises a transmission line, and a parameter of said transmission line is a function of MAP.

In a second aspect, we provide systems and methods for using the systems for estimating a ratio of SV values of a subject, comprising: a processing system comprising a processing unit and memory; wherein the processing system is designed to receive tracking sensor data from a tracking sensor data that relates to changes in arterial pressure; the processing system is designed to estimate a ratio of SV values, based upon: one or more outputs of a DFT of tracking sensor data relating to the arterial pressure; and wherein the processing system is designed to store or transmit said ratio of SV values.

Dependent features of this second aspect include: wherein the processing system is designed to determine parameters of a combined electrical model that corresponds to a cardiovascular model, by a calibration fitting of a function of the combined electrical model to a function of output of a DFT of tracking sensor data for data from a calibration time period; and wherein the system further comprises a calibration sensor; a tracking sensor; and a device for visually displaying or transmitting values for hemodynamic parameters; and wherein the processing system is designed to determine SVV from ratio of SV values.

In a third aspect, we provide systems and methods for using the systems for estimating values of hemodynamic parameters of a subject, comprising: a processing system comprising a processing unit and memory; wherein the processing system is designed to determine a calibration value for at least of MAP, PP, Ps, and Pd from calibration sensor data obtained from a subject; wherein the processing system is designed to calculate an FSUB value from a function of variables comprising: MAP; PP; and a value of a harmonic of a DFT of tracking sensor data obtained from the subject; wherein the processing system is designed to calculate hemodynamic values of at least one hemodynamic parameter using said FSUB value and said calibration value; and wherein the processing system is designed to store or transmit the calculated hemodynamic values.

In a fourth aspect, we provide systems and methods for using the systems for estimating values of hemodynamic parameters of a subject, comprising: a processing system comprising a processing unit and memory; wherein the processing system is designed to receive tracking sensor data from a tracking sensor; wherein the processing system is designed to calculate estimated hemodynamic values of a hemodynamic parameter at two or more time instances, based upon: one or more outputs of a DFT of tracking sensor data relating to the arterial pressure, which tracking sensor data was obtained from the subject during a first tracking time period;
one or more outputs of a DFT of tracking sensor data relating to the arterial pressure, which tracking sensor data was obtained from the subject during a second tracking time period; wherein the first tracking time period and the second tracking time period do not overlap in time; and wherein the processing system is designed to display, store or transmit data relating to the estimated hemodynamic values.

The dependent aspects are generally interchangeable with and applicable to all independent aspects.

Summary of Blood Pressure Measurement Systems

The term "blood pressure measurement system" refers to a processing system, at least one biometric tracking sensor, means (wires, fiber optics, or wireless transmitters and receivers) for the sensor to communicate data to the processing system, and at least one output device (monitor, audio generator, etc.). The output device can be used to display time dependent data, sound an alarm, or perform a similar function, or control some other system, dependent upon results of processing of received data. The hardware includes at least one digital processing unit and one digital memory unit for storing digital data. The processing system is configured to perform a calibration using data from both sensors. The first sensor, or calibration sensor, provides measurements from which MAP and PP can be determined. The tracking sensor, or tracking sensor, provides a time dependent signal correlated to the arterial blood pressure.

The processing system inputs temporally correlated outputs of the two sensors to determine calibration parameters useful in subsequently tracking the blood pressure over time based solely upon the output of the tracking sensor. Subsequent to determining the calibration parameters for a subject, the processing system can then be used to track blood pressure over time for that subject, using the input from only the tracking sensor.

As part of the calibration, the processing system performs a DFT of a signal from the tracking sensor, for a time interval segment corresponding to the time for one complete cardiac cycle. The processing system then applies a DC component estimating function to: (1) the value for the first harmonic output by the DFT and (2) a ratio of MAP/PP. The DC component estimating function generates a substitute DC component value. In subsequent steps of the calibration, the processing system uses this substitute DC component value instead of the zeroth order harmonic output by the DFT.

Summary of Methods

A cardiovascular model can be described with an analogous electrical model, in which current corresponds to blood flow and voltage corresponds to blood pressure.

We disclose methods comprising two generic steps. First, the processing system performs a calibration. The calibration involves data obtained from two sensors measuring certain biometric data from the same subject, calibration data from a calibration sensor, and tracking data from a tracking sensor.

The processing system uses that data to determine values for parameters of an electrical model, for that subject. Second, the processing system uses (1) the values for MAP and/or PP from the calibration; (2) values for parameters of that electrical model for that subject obtained by the calibration; and (3) values of the electrical model obtained by fitting a combined electrical model representing the cardiovascular system and a tracking sensor to the tracking sensor output, to output estimates of various values of hemodynamic parameters. These may include: MAP; PP; Ps; Ps; SV; and SVV. The processing system may also estimate hemodynamic parameters during both the first and second steps by using parameters determined for the electrical model and MAP and/or PP.

The design of the cardiovascular model described below indicates that, once calibrated for a particular subject, the outputs of the system using the cardiovascular model calibrated for that particular subject should be accurate for extended periods of time. Current data results show accuracy for a subject exists for a period of weeks. Significantly, the time period over which the model's tracking is accurate for a subject is much longer than the time typically required for a medical procedure, thereby allowing these embodiments to use a single calibration and then accurately monitor the arterial pressure of a subject for the duration of a medical procedure. However, for any subject, the calibration step may be repeated at any time to ensure continued accuracy and reliability of tracking of arterial pressure values for that subject. For example, the calibration may be repeated every: few minutes; fifteen minutes; half hour; hour; half day; day; week; month; or longer.

Summary of Calibration

FIG. 7 shows algorithm 700 comprising steps of calibrating 701 and tracking 702. Arrow exiting 702 and entering 701 indicates that the calibrating followed by tracking may be repeated. Repeating may occur once, aperiodically, or periodically, for example at intervals between 1 minute and twelve months. Number of repetitions may be zero, that is, only one calibration may ever be performed. Preferably, the system initially performs on a particular subject at least 3 or 4 calibrations closely spaced in time, such as at intervals of 1-3 minutes, followed by calibrations at larger time intervals, such as between ever 15 and 60 minutes. Calibrating step 701 and tracking step 702 are described herein below.

FIG. 17 shows flow chart 1700 comprising steps 1710 to 1770, described below.

First, Positioning

First, in step 1710, a calibration sensor and a tracking sensor are each positioned relative to a particular subject so that these sensors can obtain biometric signals from that subject. The tracking transducer is located at a position relative to the subject where it can detect an arterial pulse to provide tracking data. Such locations include adjacent the wrist, finger, arm, torso, leg, foot, head, forehead, earlobe, nose ala or cheek. In a preferred embodiment, the tracking transducer is placed on a fingertip.

Second, Obtaining Data from Both Sensors

Second, in step 1720, a processing system obtains sensor measurements from both the calibration sensor and the tracking sensor. Preferably, the processing system obtains sensor measurements from both sensors that overlap in time. The smaller the time difference between the signals from the tracking sensor and the calibration sensor that are used by the processing system to perform calibration, the higher the anticipated degree of accuracy for the resulting calibration. Preferably, the processing system stores sensor measurements in memory.

The third and fourth steps can occur in any order, but must occur before the fifth step.

Third, Determining Values from Calibration Sensor

Third, in step 1730, the processing system determines a value for MAP and a value for the ratio of PP/MAP, based upon signals sensed by the calibration sensor over a period of time. This determination may be made by circuitry adjacent the sensor's transducer or remote from the sensor's transducer. The processing system stores these values in memory.

The tracking sensor is designed to provide a time dependent signal that correlates with the time dependent arterial pressure wave at the region of the subject's arteries from which the tracking sensor receives signals.

Fourth, Processing Tracking Sensor Data

Fourth, in step 1740, the processing system separates the signals from the tracking sensor into discrete time interval segments. Each discrete time interval segment corresponds to the time for one cardiac time period. These discrete time interval segments each comprise a set of sampled values representing the particular cardiac cycle.

The processing the system determines characteristic features in the signal from the tracking sensor which it assumes corresponds to the beginning and end of a cardiac cycle. For example the system may determine times of local maxima for the signal, the time of maximal derivative within some timeframe, and the second time derivative of the signal from the tracking sensor, and use any one or more of these characteristic features to indicate end of one cardiac cycle and beginning of the next cardiac cycle. The processing system may also include identifying the extrema of a correlation of a predefined function to the signal from the tracking sensor, to determine start and end of each cardiac cycle.

In the preferred embodiment, the processing system takes tracking data from a tracking sensor for an arbitrary time period, and determines the arterial pulses contained within that period. The processing system takes the segments of the beginning and end of that arbitrary time period which it determines are not part of a complete pulse in that arbitrary time period. The tracking system connects these segments to the adjacent time period, so that all pulses are accounted for.

The system performs a Discreet Fourier Transform (DFT) on each discrete time interval segment, to provide the DFT values and corresponding frequencies, for each discrete time interval segment. This DFT results in values for the first and subsequent harmonics for that discrete time interval, H0, H1, H2, H3, etc., for each discrete cardiac time period. For calibration, it is only essential to perform DFT on values for one discrete time interval segment corresponding to one arterial pulse. However, it may be useful to perform this DFT on plural arterial pulses and use values from these plural arterial pulses. Because the duration of cardiac cycles vary from one another, it is important to retain the actual frequency values for each cardiac cycle, or equivalently, the time interval duration. Instead of retaining the actual frequency values, the processing system could store the time interval duration, or number of samples associated with each time interval duration.

A result of the fourth step is a frequency domain representation of the tracking signal, for each arterial pulse. The processing system stores frequency domain representation of the tracking signal, for each arterial pulse, in memory.

However, it is also possible, although less preferred, for the processing system to perform DFT on a discrete time segment equal to a plural cardiac cycles. (In this alternative, a corresponding electrical model is designed to represent the corresponding arterial pressure resulting from this plural of arterial pulses. The electrical model corresponding to one arterial pulse is discussed below.)

Fifth, Determine Estimated H0s of Arterial Pulses

Fifth, in step 1750, the processing system calculates a value for a DC component estimating function, FSUB. FSUB may be a function of the values, H1, H2, H3, etc., for DFT of the discrete time interval segment; and the MAP and PP values derived from the calibration sensor.

The DC component estimating function outputs a real number. The DC component estimating function may have the form:

$$FSUB = F(H1, H2, H3, \ldots, MAP, PP) \text{ where FSUB is a real number.}$$

FSUB must be a function of at least MAP, PP (from the calibration sensor's data), and at least one of the values for H1 to H10.

In some embodiments $$FSUB = F(MAP, PP, \text{ and } H1) = H1^* \{K^*(MAP/PP) + \xi^* MAP\}, \text{ where:} \quad (2)$$

$\xi$ is in the range of −0.2 to 0.2; and
K is between 3 and 8.

Preferably, K is 5.56 plus or minus thirty percent, and in a preferred embodiment is 5.56. Preferably, $\xi$ is between −0.01 and 0.01, and more preferably zero.

The absolute value of FSUB/H1 of a subject varies between 1 and 100. This ratio changes for each cardiac cycle of a subject, and also differs subject to subject. (FSUB is real. H1 may be complex.) The processing system stores the calculated values for the DC component estimating function, FSUB, for pulses, in memory.

Sixth, Normalize the DFT of the Values Obtained from the Tracking Sensor, Using the Value Determined for FSUB Sixth, in step 1760, the processing system divides the values for H1, H2, H3, etc. of the DFT from the tracking signal for one arterial pulse, by the value for FSUB, and preferably stores the results in memory. This normalizes H1, H2, H3, etc., for the tracking signal, to the FSUB value. This provides a normalized output MEASURE1. MEASURE1 does not include a value for the zero harmonic (corresponding to a DC value in time domain). MEASURE1 includes the normalized values of H1, H2, H3, etc.

Seventh, Fitting Output of a Model to the Normalized Output

An output of such an analogous electrical model (corresponding to a cardiovascular model) represents arterial pressure in the region of the subject sensed by the tracking transducer. An output of a combined electrical model combining such an electrical model and a model of a tracking sensor coupled to arterial pressure at some location in a subject, provides an output of the tracking sensor.

The processing system is configured to determine parameters of a combined electrical model by fitting the model to normalized output.

In some embodiments, the electrical model comprises a model time constant, τ, which models a time constant of a cardiovascular system. In some embodiments, the electrical model comprises a parameter Ts, which represents a time difference between when Systole begins and a determined time at which the corresponding cardiac cycle begins.

MODEL1 is the combined electrical model normalized by multiplying values of the output of the combined electrical model by a constant such that the value at zero frequency of the resulting MODEL1 is unity.

Seventh, in step 1770, the processing system performs a fitting between (1) the output of MODEL1 and (2) MEA-SURE1. This fitting is performed by minimizing differences between two functions evaluated at one of more of the harmonic frequencies H1, H2, H3, etc., preferably evaluated at least two harmonic frequencies, and in a preferred embodiment at the H1, H2, and H3 frequencies. Fitting provides one set of parameters of the model for whatever frequencies are evaluated. One function is the output of the combined electrical model. The other function is the MEA-SURE1. The domain values for each function are the same harmonic frequencies determined for the corresponding arterial pulse.

Fitting of the combined electrical model to the MEA-SURE1 results in values of parameters of the electrical model. The processing system stores these values of parameters of the electrical model in memory.

The processing system may perform the foregoing minimization for a plurality of arterial pulses time correlated to when the processing system used data from the calibration sensor to obtain MAP and/or PP values. The processing system may use one or more of the sets of parameters obtained by these minimizations to arrive at representative values for these parameters. For example, the processing system may discard or reduce the weight of parameters that are relatively extreme compared to corresponding values from other arterial pulses. Consequently, for each calibration relying upon a MAP and/or PP value, the processing system determines one final set of parameters for the electrical model.

Fitting, such as least squares fitting and algebraic fitting are old and well known in the art. Fitting minimizes some measure of the difference between two functions over an interval, such as the square of the difference of the functions at each point. Algorithms to fit functions to data signals are old and well known. The fitting results in values for the parameters of the electrical model that are specific to the particular subject from which the data was received. These personal model parameter values result in a model calibrated to that subject. Determining a subject's personal model parameter values completes the calibration, for that subject, and for the specific MAP value obtained from the calibration sensor. Conventional numerical method is used to perform the fitting.

In some embodiments, the processing system minimizes error function, "err", which is defined as follows (and is a measure of the difference in values of the combined electrical model to the MEASURE1):

$$\text{err} = W \circ \text{abs}\left(\frac{MODEL_1(H)}{MEASURE_1(H)} - 1\right), H = 1, 2, \quad (3)$$

where "∘" represents the dot product operator;
H represents the harmonic number; and
W is a weighting function. W may have values (1; 0.5 to 15; 0.3 to 50, and any real number for higher harmonics). Preferably, W has values in the range (1; 0.5 to 5; 2 to 20, and any real number for higher harmonics). W may have values: (1, 1, 1); (1, 2, 4); (1, 1.2, 4); (1, 1.2, 6); (1, 1.3, 9); (1, 1.2, 12); and (1, 1.1, 14), and zero for all higher harmonics.

The interval of time over which the data from the tracking sensor was used in the calibration does not necessarily have to overlap with the interval of time over which the calibration sensor data was used to determine a value for MAP. For example, if the subject's arterial pressure variations over cardiac cycles remain very stable over time, then offsets in the time intervals for obtaining a MAP value and the time interval for obtaining the data from the tracking sensor used in the calibration may not substantially change the resulting determination of parameters of the model. However, the closer in time to one another are those two time intervals, the more accurate calibration of the model. Preferably, the interval of time over which the data from the tracking sensor was used in the calibration and the interval of time over which the calibration sensor data was used to determine the value for MAP have at least some overlap. More preferably, interval of time over which the data from the tracking sensor was used in the calibration and the interval of time over which the calibration sensor data was used to determine the value for MAP overlap have greater than a 50 percent overlap, even more preferably a 90 percent overlap, and most preferably are (within the accuracy of sampling rates for the sensors) identical.

Thus, the seventh step results in representative values of parameters of the electrical model obtained using data for one or more arterial pulses.

The processing system may implement an algorithm to perform a quality check on tracking sensor signal to reject outlier arterial pulses from use in calibration.

Consequently, the calibration of the model is completed when one set of parameters for the electrical model based upon MAP and/or PP values provided by the calibration sensor is completed.

Tracking Arterial Pressure

After a calibration is completed for a particular subject, the system can use (1) the values for parameters of the electrical model stored in memory during calibration; (2) the MAP and/or PP values stored in memory during calibration; and (3) the signal from the tracking sensor, to estimate arterial pressure values versus time, for that subject. The processing system continuously receives data from the tracking sensor, and performs pulse by pulse operations to estimate MAP and/or PP on a pulse by pulse basis. Pulses in this paragraph refer to arterial pulses. Pulse by pulse herein indicates that the processing system estimates values for MAP and/or PP on individual pulses. Optionally, the processing system estimates other hemodynamic parameters using the pulse by pulse determinations. The processing system may store in memory, transmit, or both, the resulting estimate MAP and/or PP, and estimate arterial pressure values versus time.

After calibration, the tracking sensor remains in a position capable of detecting arterial pressure. As in calibration step 2, the tracking provides a time dependent signal that correlates with the time dependent arterial pressure wave at the region of the subject's arteries from which the tracking sensor receives signals During tracking, as in the fourth step of calibration, the processing system separates the signals from the tracking sensor into discrete time interval segments. Each discrete time interval segment corresponds to the time for one complete cardiac cycle. These discrete time interval segments each comprise a set of sampled values representing the particular cardiac cycle. The system performs a Discreet Fourier Transform (DFT) on each discrete time interval segment, to provide the DFT values and corresponding frequencies, for each discrete time interval segment. This DFT results in values for the first and subsequent harmonics for that discrete time interval, H0, H1, H2, H3, etc, for each cardiac time period. Because the duration of cardiac cycles vary from one another, it is important to retain the actual frequency values for each cardiac cycle, or equivalently, the time interval duration. Instead of retaining the actual frequency values, the processing system could store the time interval duration, or number of samples associated with each time interval duration.

A result of the fourth step is a frequency domain representation of the tracking signal, for each arterial pulse. However, as in calibration, it is also possible, although less preferred, for the processing system to perform DFT on a discrete time segment equal to a plural cardiac cycles. (In this alternative, a corresponding electrical model is designed to represent the corresponding arterial pressure resulting from this plural of arterial pulses. The electrical model for one arterial pulse is discussed below.)

Preferably, the processing system uses no more than the first five harmonics in normalization and/or fitting; preferably the processing system only uses data for harmonics below 20 Hz.

FIG. 18 shows a flow chart 1800 showing steps for tracking arterial data including steps 1810 to 1880.

At 1810, the processing system may determine which normalization to use.

The following two alternatives for performing normalization and fitting are described:

First Normalization and Fitting Method

First Normalization

During tracking, at 1820, as in the fifth step in calibrating, the processing system calculates a value for a DC component estimating function, FSUB, for at least one arterial pulse, and preferably for all arterial pulses.

FSUB may be a function of the values, H1, H2, H3, etc., for DFT of the discrete time interval segment; and the MAP and PP values previously derived from values determined by the calibration sensor. For each arterial pulse, the processing system determines an FSUB value. The processing system divides values for H1, H2, H3, etc., of that arterial pulse, by this FSUB value for that arterial pulse. This results in normalized harmonic values for the corresponding arterial pulse.

Alternatively to using a single pair of MAP and PP values from one calibration, the processing system may calculate average values for MAP and PP from plural calibrations, or may calculate weighted average values for MAP and PP from plural calibrations. For each arterial pulse, the processing system then uses these average values of MAP and PP, and the corresponding H1, H2, H3, etc., values for that arterial pulse, to determine a value for FSUB for that pulse. The processing system then divides the values for H1, H2, H3, etc., of that arterial pulse, by this FSUB value for that arterial pulse. This results in normalized harmonic values for the corresponding arterial pulse.

First Fitting Using as MODEL1

During tracking, at 1830, similar to the seventh step of calibrating, the processing system performs a fitting between (1) the output of MODEL1 and (2) normalized harmonic values for the corresponding arterial pulse, at the harmonic frequencies for that arterial pulse. Herein after, the normalized harmonic values for the corresponding arterial pulse, at the harmonic frequencies for that arterial pulse, are referred to as "MEASURE1"

The processing system performs the fitting by minimizing differences between the MEASURE1 and MODEL1. The differences may be calculated at one or more of the harmonic frequencies H1, H2, H3, etc., preferably at two or more harmonic frequencies, and in a preferred embodiment at harmonic frequencies H1, H2, and H3.

The particular electrical model employed for calibration and fitting contains plural parameters. During the fitting occurring for tracking, some parameters of the electrical model that were determined during the calibration process, are held constant.

Preferably, τ and Ts are held constant during fitting for tracking.

Fitting of the MODEL1 to MEASURE1, for an arterial pulse, results in values of parameters of the MODEL1, for that arterial pulse. The result of this fitting are multiplicity of sets of values of parameters for MODEL1, one set per arterial pulse.

Second Normalization and Fitting Method

Alternatively to the First Normalization, at 1860, the processing system performs a second Normalization.

Second Normalization

Unlike during calibration, the processing system does not normalize to the DC component of the calibration signal. Instead, the processing system divides the value for H1, H2, H3, etc. of the DFT from the tracking signal for arterial pulse, by the magnitude of the value for H1. This normalizes H1, H2, H3, etc., for the tracking signal. Herein after, these normalized values and corresponding frequencies are called "MEASURE2." MEASUSRE2 values may be complex. The magnitude of the fundamental harmonic of MEASUSRE2 is by definition unity (H1 divided by the magnitude of H1).

Second Fitting

During tracking, at 1870, similar to the seventh step of calibrating, the processing system performs a fitting between the output of a combined electrical model, referred to herein after as MODEL2, and MEASURE2."

MODEL2 is the combined electrical model normalized by multiplying values of the output of the combined electrical model by a real valued constant such that the magnitude of its first harmonic value is unity.

The processing system performs fitting on a predefined number of harmonics, excluding the zero (DC) Harmonic. The processing system may calculate differences at one or more of the harmonic frequencies H1, H2, H3, etc, preferably at two or more harmonic frequencies, and in a preferred embodiment at harmonic frequencies H1, H2, and H3. In a preferred embodiment, the processing system performs fitting at H1, H2, and H3.

The particular combined electrical model employed for calibration and fitting contains plural parameters.

For this second fitting alternative, some parameters of the electrical model that were determined during the calibration process, are held constant for fitting during tracking. Preferably, τ and Ts are held constant during this fitting.

Fitting of the MODEL2 to MEASURE2, for an arterial pulse, results in values of parameters of the MODEL2, for that arterial pulse. The result of this fitting are multiplicity of sets of values of parameters for MODEL2, one set per arterial pulse. In some embodiments, fitting of MODEL2 TO MEASURE2 uses an error function like "err" except that MODEL2 and MEASURE2 replace MODEL1 and MEASURE1.

The processing system may use the values of a parameters of a model, for an arterial pulse, and that model, to estimate values representing biometric parameters of the subject. These include Ps, Pd, MAP, SV per arterial pulse, diameter, length, and stiffness of the Aorta, and heart pumping energy per arterial pulse, heart elastance, heart unloaded volume, end-systolic volume, and end-diastolic volume.

Eighth, Estimating MAP

At 1840, the processing system uses one of the following two alternatives for estimating MAP:

First Method of Estimating MAP

The processing system estimates one or more values for MAP, for an arterial pulse, to be the result of a function of values comprising values for $w_0$calib; MAPcalib; and $w_0$est. One such estimate of MAP for a pulse is MAPest, which is defined as follows:

$$MAPest = F(w_0\text{calib};MAPcalib; \text{ and } w_0\text{est}). \quad (4)$$

$w_0$calib is the representative value of one particular model parameter obtained from fitting during a particular calibration. The phrase "representative value" in this paragraph refers to the representative values discussed for the seventh step of calibration.

MAPcalib is the value for MAP obtained during calibration for that particular calibration.

$w_0$est is the value of the same particular electrical model parameter obtained from fitting of tracking data for an arterial pulse.

Preferably, the processing system estimates MAPest by computing a value for the function:

$$MAPest = MAPcalib*P(w_0\text{est})/Q(w_0\text{est})*Q(w_0\text{calib})/P(w_0\text{calib}). \quad (5)$$

P represents a polynomial.
Q represents a polynomial.
In one embodiment, $$P(x)=K2*x2+K3x3 \text{ and } Q(x)=K4, \quad (6)$$

where K2, K3, and K4 are coefficients, and "**" means "to the power". K2, K3, and K4 have predetermined fixed values.

In a currently preferred embodiment, $$P(x)=x*x \text{ and } Q(x)=1. \quad (7)$$

In this embodiment, K2=1, K3=0 and K4=1. K2, K3, and K4, may be subject dependent. For subject dependence, the processing system may determine K2, K3, and K4 by determining values for K2, K3, and K4, that minimizes error between measured MAPest determined using different calibrations. For example, differences for values of MAPest for an arterial pulse, as determined by different MAPCalib values from different calibrations may be calculated, and then squared. The processing system may then determine K2, K3, and K4 values that minimize that sum. This process may be extended to data for values of MAPest for plural arterial pulses.

Another estimate of MAP for an arterial pulse is MAPout (n), which is defined below.

The processing system may filter MAPest outliers. For example, the processing system may filter MAPest to compute MAPout(n). For example, by performing the following exponential filter on values for MAPout.

$$MAPout(n)=ff*MAPout(n-1)+(1-ff)*MAPest(n) \quad (8)$$

Where: n is an index that identifies a sequence of arterial pulses; MAPout(n) is the output of the function for the nth arterial pulse; ff is a forgetting factor whose value is between 0 and 1 and preferably between 0.8 and 0.98; and most preferably between 0.9 and 0.95; MAPout (n−1) is the value of MAPout for the pulse n−1; and MAPest(n) is the value for MAPest for pulse n.

The processing system may filter the input value to MAPout by removing values of MAPest that are outliers. That is, suspect due to their relatively large difference from some normative value or range for MAP.

Second Method of Estimating MAP

The processing system estimates one or more values for MAP, for an arterial pulse, to be the result of a function of values comprising values for a multiplicity of calibrations $w_0\text{calib}[i]$; $\text{MAPcalib}[i]$; and $w_0\text{est}$, where $i=1, \ldots, n$. One such estimate of MAP for a pulse is MAPest2, which is defined as follows:

$$\text{MAPest2} = F(w_0\text{calibs}; \text{MAPcalibs}; \text{and } w_0\text{est}), \text{ where:} \quad (9)$$

$w_0\text{calibs}$ is a vector, that is a series of values $w_0\text{calib}[i]$, $i=1, \ldots, n$;

MAPcalibs is a vector, that is a series of values $\text{MAPcalib}[i]$, $i=1, \ldots, n$; and $w_0\text{est}$ is defined above.

$w_0\text{calib}[i]$, $i=1, \ldots, n$ are each a representative value of one particular model parameter obtained from fitting for each one of the n calibrations. The phrase "representative value" in this paragraph refers to the representative values discussed for the seventh step of calibration.

Preferably, the processing system estimates MAPest2 by computing a value for the function:

$$\text{MAPest2} = (P(w_0\text{est})/Q(w_0\text{est}))\text{times: AVG(MAPcalib} [i]*Q(w_0\text{calib})/P(w_0\text{calib})). \quad (10)$$

AVG( ) is an operator representing weighted averaging

P and Q each represent a polynomial and $w_0\text{est}$ and $w_0\text{calib}$ are defined above. (Polynomial Q does not represent the same quantity as Q specified as a parameter of an electrical described herein.)

In one embodiment:

$$P(x) = K2*x^{}2 + K3\, x^{}3 \text{ and } Q(x) = K4, \quad (11)$$

where K2, K3, and K4 are coefficients; and "**" means "to the power"; K2, K3, and K4 have predetermined fixed values; and $$\text{AVG} = (1/n)*(\text{sum(MAPcalib}[i]*(w_0\text{calib})/P(w_0\text{calib}))), \quad (12)$$

where "sum( )" means the sum of all elements in the argument.

In a currently preferred embodiment, $$P(x) = x*x \text{ and } Q(x) = 1. \quad (13)$$

In this embodiment, K2=1, K3=0 and K4=1;

$$\text{AVG}(x) = f\!f2*x[-n] + f\!f2^{**}2*x[n-1] + \ldots + f\!f2^{**}n*x[1], \text{ where:} \quad (14)$$

** stands for "to the power of" and $f\!f2$ is a number between 0 to 1. (15)

Preferably ff2 is between 0.3 to 0.7 an more preferably ff2 is between 0.45 to 0.55

Another estimate of MAP for an arterial pulse is MAPout2(n), which is defined below.

The processing system may filter MAPest2 outliers. For example, the processing system may filter MAPest2 to compute MAPout2(n). For example, by performing the following exponential filter on values for MAPout2.

$$\text{MAPout2}(n) = f\!f*\text{MAPout2}(n-1) + (1-f\!f)*\text{MAPest2}(n) \quad (16)$$

Where: n is an index that identifies a sequence of arterial pulses; MAPout2(n) is the output of the function for the nth arterial pulse; ff is a forgetting factor whose value is between 0 and 1 and preferably between 0.8 and 0.98; and most preferably between 0.9 and 0.95; MAPout2(n−1) is the value of MAPout2 for the pulse n−1; and MAPest2(n) is the value for MAPest2 for pulse n.

The processing system may filter the input value to MAPout2 by removing values of MAPest2 that are outliers.

That is, suspect due to their relatively large difference from some normative value or range for MAP.

Ninth, Estimating PP

At 1850, the processing system performs one of the following alternatives for estimating PP.

First PP Estimation Method:

The first PP estimation method estimates the PP of a particular arterial pulse. This particular pulse is called the estimated arterial pulse. The first PP estimation method estimates PP2 of the particular arterial pulse from a function of the PP of another arterial pulse. This equation is:

$$PP2 = PP1 * \frac{MAP2}{MAP1} * \sqrt{\frac{(\tau_1 * w_1)^2 + 1}{\left(\tau_1 * \frac{MAP_2}{MAP_1} * w_2\right)^2 + 1}} \quad (17)$$

where:

PP2 is the PP of the particular arterial pulse; PP1 is the PP of the other arterial pulse; MAP2 is a value for MAP of the particular arterial pulse determined in the eighth step; MAP1 is the MAP of the other arterial pulse;

$$w1 = \frac{2*\Pi}{IBI_1} \quad (18)$$

$$w2 = \frac{2*\Pi}{IBI_2} \quad (19)$$

$\tau_1$ is a time constant that can be calculated by:

$$\tau_1 = \sqrt{\frac{K^2 * \left(\frac{MAP_1}{PP_1}\right)^2 - 1}{w_1^2}}, \quad (20)$$

where K is the constant defined above

Where: $\Pi$ is the mathematical constant (ratio of circumference to diameter); "j" is the imaginary number (square root of minus 1); $IBI_1$ is the cardiac time period of the other arterial pulse; and $IBI_2$ is the cardiac time period of the particular arterial pulse.

PP2 is the estimate of PP resulting from the first PP estimation method.

Second PP Estimation Method

The second PP estimation method estimates the PP of the particular arterial pulse, from a function of the PP of another arterial pulse, as follows:

using a different equation:

$$PP2 = PP1*MAP2/MAP1, \text{ where:} \quad (21)$$

PP2 is the estimate of PP for the particular arterial pulse; PP1 is the PP of the other arterial pulse; MAP2 is the MAP of the particular arterial pulse determined in the eighth step; and MAP1 is the MAP of the other pulse.

PP2 is the estimated PP resulting from the second PP estimation method.

Tenth, at 1880, the processing system estimates Ps and/or Pd.

The processing system may estimate Ps and/or Pd from PP and MAP using functions of MAP and PP. Generally:

Ps=F(MAP, PP); and

Pd=F(MAP, PP).

The conventional choices for these two functions are:

$$Ps = MAP + \tfrac{2}{3} * PP \quad (22)$$

$$Pd = MAP - \tfrac{1}{3} * PP. \quad (23)$$

In one embodiment, MAP is the result of eighth step, and PP is the result of the ninth step.

SV Determination and SVV Estimation

FIG. 19 shows a flow chart 1900 containing steps 1910-1980, described below, for estimating SV.

The processing system determines a relative value for SV on a pulse by pulse basis. The ratio of SV for any two pulses is a measure of SVV. Statistical variations in plural SVs can be determined by ratios of SVs from plural pulses. These statistical variations are measures for SVV. Typically, SVV refers to a normalized standard deviation representing standard deviation of SV for a number of arterial pulses, divided by the mean of these SVs. The processing system determines a value for SVV by calculating this normalized standard deviation.

The processing system determines a relative value for SV on a pulse by pulse basis, as follows. After acquiring tracking data for a period of time corresponding to a sequence of arterial pulses, as discussed above, the processing system uses characteristic features in the signal to determine times corresponding to the start time for each one of a train of arterial pulses.

The processing system determines coefficients of a model where a forcing function is used as the system excitation. The forcing function represents current in an electrical model and corresponds to blood flow exiting the heart of a subject. The coefficients correspond to the effect of the transmission of the blood from the heart to the position from which the tracking sensor obtains data. The processing system equates the linear combination of coefficients and values of a forcing function to the tracking data. The forcing function and the tracking data may be represented in either time domain or frequency domain. The unknowns in the equations are the (real number) values for the SVs. The result in either case is a series of coupled linear equations, which can be solved in a conventional manner, to determine relative values for the sequence of SVs. The model assumes that there is a fixed (that is pulse independent), but unknown time difference, between times at which a characteristic feature (e.g., maxima, or maxima in some power of the derivative) exists in the forcing function and the cardiac cycle start times. Requiring SVs to be real enables this time difference to be determined and the equations to be solved. Solving in the frequency domain is preferred, but the processing system could also solve in time domain. The solution process for SV below relies on linear algebra, and uses matrix inversion to solve the set of equations formulated below. Other methods such as Gaussian elimination, Kramer's method, LU decomposition, Levinson recursion, etc. may also be used.

SV estimation step 1: At 1910, the processing system determines sequential cardiac cycle start times in tracking sensor data. The processing system selects n adjacent start times. These start times are: T1, T2, ..., Tn. The total duration of the n cardiac cycles defines a time segment, Tseg=T(n+1)−T(1). The corresponding sequence of SVs are referred to herein below as SV(i), for i=1 to n.

At 1920, SV estimation step 2: At 1920, the processing system Fourier transforms the tracking sensor data for a period of time corresponding to a sequence of arterial pulses. The result of this step are a series of values and corresponding frequencies. The frequencies are 0, 1/Tseg, 2/Tseg, ....

SV estimation step 3: At 1930, the processing system selects n frequencies to be used in the SV estimation, where n is the number of cardiac cycles determined in SV estimation step 1. Preferably, the n frequencies are [(n−n//2)/Tseg, (n−n//2+1)/Tseg, ... n/Tseg, (n+1)/Tseg ... (n+n//2−1)/Tseg)] where the symbol "//2" means "integer division," by 2, which is division by 2 in which any remainder is ignored.

SV estimation step 4: At 1935, the processing system evaluates the frequency response of some electrical model representing the relationship between SV and arterial pressure of a subject. Preferably, this electrical model is the electrical model used for calibration. Preferably, the parameters in this electrical model are the parameters determined during from calibration when fitting the output of the electrical model to the normalized output MEASURE1. The processing system evaluates this electrical model at the frequencies determined in SV estimation step 3. The results are values of the frequency response at these frequencies.

SV estimation step 5: At 1940, the processing system divides each value of the Fourier transform obtained from SV estimation step 2 by the corresponding model response value. The result is an ordered sequence of n values that are a ratio of the actual data divided by model data for the n frequencies determined in step 2. Call this ordered sequence vector "R."

SV estimation step 6: At 1950, the processing system determines the values of an n by n matrix M. The first row of Matrix M contains values that are the Fourier Transform of a sequence of Dirac delta functions at a first frequency w1, of the n frequencies selected in SV estimation step 3. The first row and first column element of M, is M(1,1). M(1,1) stores the value of the Fourier Transform of the first Dirac delta function at frequency w1. M(1,2) stores the value of the Fourier Transform of the second Dirac delta function at frequency w1, etc. M(2,1) stores the value of the Fourier Transform of the first Dirac delta function at frequency w2. M(2,2) stores the value of the Fourier Transform of the second Dirac delta function at frequency w2, etc. M(n,n) stores the value of the Fourier Transform of the last Dirac delta function at frequency wn. M(i,k) stores exp(−j*Tk*wi).

In the preferred embodiment the processing system inverts this matrix M to determine matrix invM.

SV estimation step 7: At 1970, the processing system determines a value, deltaT, which minimizes the imaginary part of Z in the matrix equation:

$$Z = invM * invL(\text{delta}T, \ldots) * R, \text{ where:} \quad (24)$$

$$Z \text{ is } n \text{ by } 1 \text{ matrix of complex values;} \quad (25)$$

invL is an n by n diagonal matrix having matrix values exp(j*deltaT*w1) at position 1, 1; exp(j*deltaT*w2) at position 2,2, ..., exp(j*deltaT*wn) at position n,n; deltaT is an unknown having a real value; and R is the ordered sequence vector defined above.

Preferably, the processing system performs a minimization algorithm that minimizes an error function that is a function of the values of the components of Z, to determine the value of deltaT. However, deltaT may also be determinable by direct solution methods, for example linear algebra methods. One suitable error function is:

$$\text{Err}=\text{sum}(im(Z(i))**2) \text{ where:} \quad (26)$$

"**" means "to the power";
im( ) means the imaginary part;
sum( ) means the sum of all the arguments; and
Z(i) is ith value for Z.

Suitable minimization algorithms are well known, and include L-BFGS-B, Nelder-Mead, Powell, conjugate gradient, BFGS, Newton-conjugate gradient, truncated Newton algorithm, Constrained Optimization BY Linear Approximation, Sequential Least Squares Programming, and Differential Evolution.

The result of SV estimation step 7 is a value for deltaT.

SV estimation step 8: At 1980, the processing system substitutes the value for deltaT found in SV estimation step 7 in invL as defined in SV step 7, calculates $$SV=\text{real}(invM*invL*R), \text{ where:} \quad (27)$$

SV is an ordered sequence of the components SV(i), i=1 to n;
real( ) is an operator that determines the real part of each of the argument's components; and R the ordered sequence vector defined above.

The processing system can use the values of the components of SV to calculate SVV.

Fitting to Tracking Data Spanning Plural Cardiac Cycles

The processing system can perform DFT of tracking data for a discrete time segment equal to plural cardiac cycles. In this case, the driving function of the electrical model represents the driving function having that plurality of pulses. Each one of these cardiac cycles has a specific SV associated with it. In this case, the processing system may use the SV estimation method to set the amplitude of the driving function for each pulse.

Preferred System and Method

A preferred method uses an automated Sphygmomanometer to measure Ps and Pd of a subject. Automated Sphygmomanometer typically use an oscillometric method for measurement. Automated Sphygmomanometers pressurize and then depressurize a cuff, or vice versa, and take measurements of blood pressure as the cuff deflates or inflates. Automated Sphygmomanometers determine one value for Ps, one value for Pd, and one value for MAP, based upon data captured during cuff inflation or deflation, which occurs over a series of (more than one) cardiac cycles. The time period over which a an automated Sphygmomanometer takes data to determine a value for Ps, or for Pd, or for MAP (or any combination of such values), is normally on the order of ten seconds, which normally corresponds to about 10 cardiac cycles of the subject.

Preferably, a tracking sensor provides a tracking signal from the same subject during the time period over which the Sphygmomanometer receives data from which the Sphygmomanomete determines Ps, Pd, and/or MAP for that subject.

Preferably, a single device hardware receives both the automated Sphygmomanometer's data and the tracking sensor's signal. In one embodiment, the single hardware device is a PCM. Conventional PCMs typically receive various biometric signals measured from a human, including signals indicative of heart beat and blood oxygen level, and provide a time dependent visual display of those biometric parameters.

U.S. provisional 62/609,435 titled "Estimating the relationship between MAP value and pulse amplitude and methods to achieve so," discloses one method for estimating Ps and Pd for an individual arterial pulse, from a known value for MAP for that arterial pulse and the waveform for that arterial pulse, and known values for Ps and Pd for one arterial pulse.

After calibration, tracking sensor data is used to estimate MAP, Ps, and Pd for each arterial pulse The system also includes an estimator for SVV derived from the signal provided by the tracking sensor.

DETAILED DESCRIPTION OF EMBODIMENTS

Figure 1:
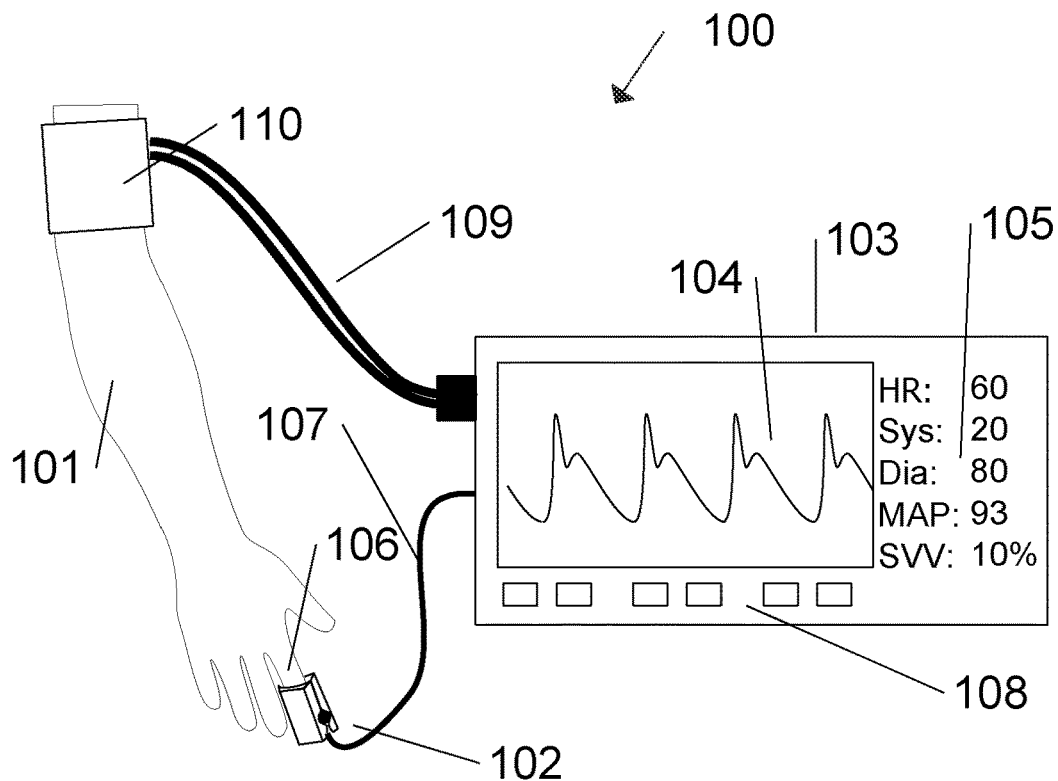
FIG. 1 shows system 100, which is a first embodiment of the invention, and an interrelationship of system 100 with a limb of a subject.

FIG. 1 shows system 100 of a first embodiment and their structural interrelationship with arm 101 of a subject. System 100 comprises PCM 103, cuff 110, and tracking transducer 102.

Tracking transducer 102 comprises a PPG transducer and is mounted on a subject's finger 106. Cable 107 connects tracking transducer 102 to PCM 103. Cuff 110 is mounted around a subject's arm. Two tubes 109 connect cuff 110 to PCM 103. Cuff 110, tubes 109, and PCM 103 comprise an oscillometric cuff based sphygmomanometer. Preferably, tracking transducer 102 obtains signals from a region of the subject whose blood flow is not cut off by cuff 110, such as a finger on the opposite are as the cuff.

PCM 103 comprises display 104 and user controls 108.

Display 104 can preferably display graphic representation of biometric data versus time 104. Biometric data versus time, as shown in FIG. 1, may include arterial pressure. Display 104 can preferably display numerical data 105 representing time averages of biometric data. Numerical data 105, as shown in FIG. 1, may include Heart Rate (HR), Ps, Pd, MAP, and SVV.

Controls 108 preferably enable a user to program PCM 103 to graphically display different biometric data versus time (such as ECG and/or pressure wave), change the time scale of the graphic display, and change the time or number of arterial pulses used to obtain the time averaged numerical data 105. Controls 108 may also be used to control time delays between sequential calibrations, or to activate immediate calibration.

PCM 103, tubes 109, and cuff 110 enable measurement of pressure variations, from which Ps, Pd and MAP can be estimated. Measurement of Ps typically occurs a few seconds to less than a minute prior to or after measurement of Pd, as the cuff deflates or inflates. Preferably, PCM 103 is programmed to determine from the cuff based measurements, a value for MAP, a value for Ps, and a value for Pd.

PCM 103 comprises at least one numerical processor, such as an Intel™ 17 processor. Preferably, this at least one processor executes mathematical algorithms on data transduced by cuff 110 and tracking transducer 102. Preferably, this at least one processor determines one or more of HR, Ps, Pd, MAP, and SVV numerical values, and arterial pressure wave, as shown in display 104, from data transduced by cuff 110 and tracking transducer 102.

Figure 2:
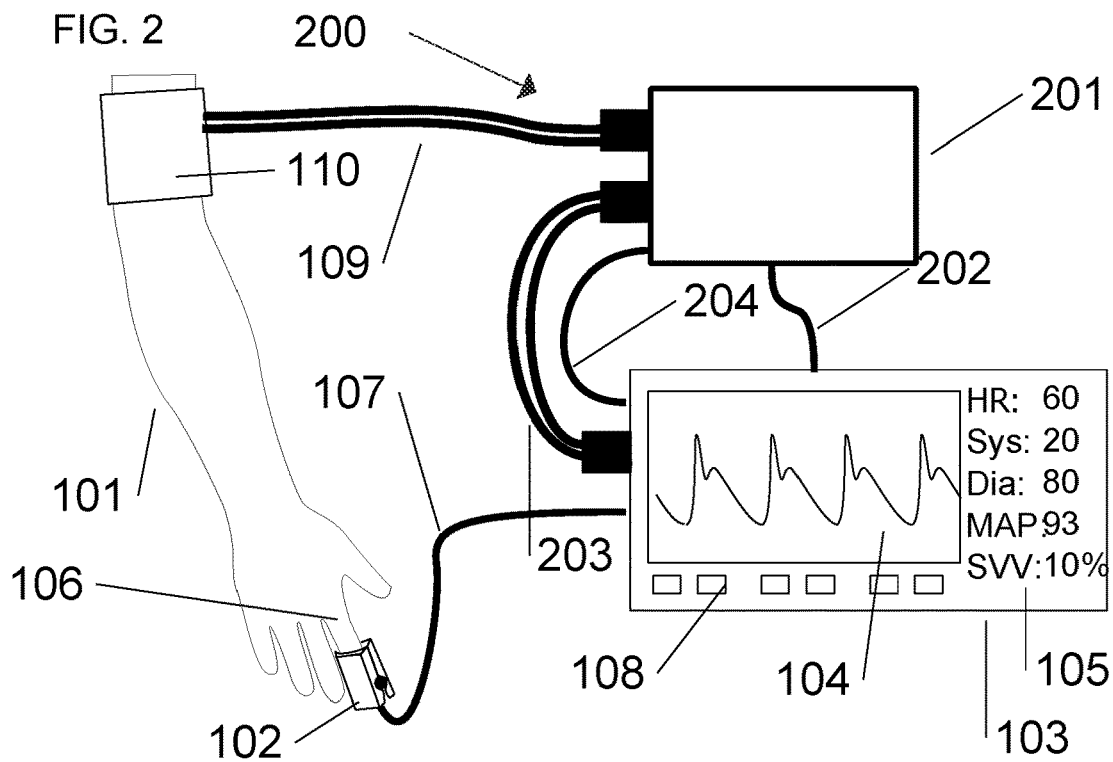
FIG. 2 shows system 200, which is a second embodiment of the invention, and an interrelationship of system 200 with a limb of a subject.

FIG. 2 shows physical components of a system 200 and arm 101 of the subject. System 200 comprises hardware assembly 201, and PCM 103.

Hardware assembly 201 comprises an enclosure separate from an enclosure of PCM 103. Cable 107 connects tracking transducer 102 to PCM 103. Alternatively, cable 107 may contain a branch that has one side from the branch connecting to hardware assembly 201 and the other side from the branch connecting to PCM 103. Tubes 109 connect cuff 110 to hardware assembly 201. Two tubes 203 connect hardware assembly 201 to PCM 103. These tubes communicate pressure between cuff 110 and PCM 103. Alternatively, tubes 109 may contain branches to communicate pressure directly to both hardware assembly 201 and PCM 103.

Electrical connection 202 connects hardware assembly 201 to PCM 103. Electrical connection 202 provides unidirectional (from PCM 103 to hardware assembly 201) or bidirectional communication between hardware assembly 201 to PCM 103.

In the case of unidirectional communication from PCM 103 to hardware assembly 201, hardware assembly 201 receives from PCM 103 calibration sensor values (such as values determined from data from cuff 110) and optionally the tracking sensor values (such as values generated by tracking transducer), and optionally uses electrical connection 204 to communicate the estimated pressure wave to the PCM. Wires 204 comprises four wires for an analog connection. Wires 204 provide arterial pressure values to PCM 103, for example to be displayed.

In case of bidirectional communication between hardware assembly 201 and PCM 103, electrical connection 202 may also send data to the PCM 103. Electrical connection 202 may send to PCM 103 any one or more of data derived from the calibration sensor (cuff 110) and tracking transducer 102 for display on PCM 103. Designs of PCM interfaces to convert data to desired output data formats, such as the data formats required by any particular PCM model, are well known. The particular data format required for any particular PCM may be proprietary to any particular PCM manufacturer. However, given that proprietary format, programming or designing of an interface, such that communicates over electrical connection 202, is well within the ability of anyone skilled in the art and a matter of routine engineering and programming.

Data transferred from hardware assembly 201 to PCM 103 may include any value for display by PCM 103, including time dependent traces and numerical data. Regarding alerting a person within the presence of the PCM or hardware assembly 201, alerts may be based upon biometric conditions of the subject, or determinations that biometric data is unreliable. For example, hardware assembly 201 or PCM 103 may apply reliability algorithms, which determine when biometric data indicates unreliability. For example, unreliability may be indicated by a low signal to noise ratio of the output signal of the tracking sensor; relatively large changes in data derived from sequential cardiac time periods; failure of matching of an arterial pulse to a model thereof (for example due to lack of convergence of a numerical approximation algorithm). Alerts, for example, may include a sound or visual indicator, and optionally a sound or visual indication of the specific reason for the alert.

PCM 103 of FIG. 2 is similar to PCM 103 of FIG. 1, but also comprises a port connected to line 202, for communicating data to hardware assembly 201 from PCM 103. This port serves the purpose of reading the calibration sensor values and optionally also tracking sensor values from the PCM. In another embodiment, this connection enables communication of estimated BPV values, BPV trace values and alerts, from the hardware assembly 201 to PCM 103, via wire 202.

Hardware assembly 201 processes the signals it receives from cuff 110 and tracking transducer 102, and optionally signals it receives from PCM 103, to generate a digital signal representing arterial pressure for the subject.

Alternatively, wireless transmitters may replace the wires described above for the first and second structural embodiments.

Alternatively, a complete sphygmomanometer (including means for pressurizing and deflating a cuff) may replace cuff 110 described above for the first and second structural embodiments, and wire or wireless transmitters and/or transceivers may couple this complete sphygmomanometer to PCM 103, or PCM 103 and hardware assembly 201. In this alternative, elements of a sphygmomanometer in PCM 103 and hardware assembly 201 are not required.

In the first and second structural embodiments, preferably, PCM 103 comprises the pressure driving elements of the sphygmomanometer.

Figure 3:
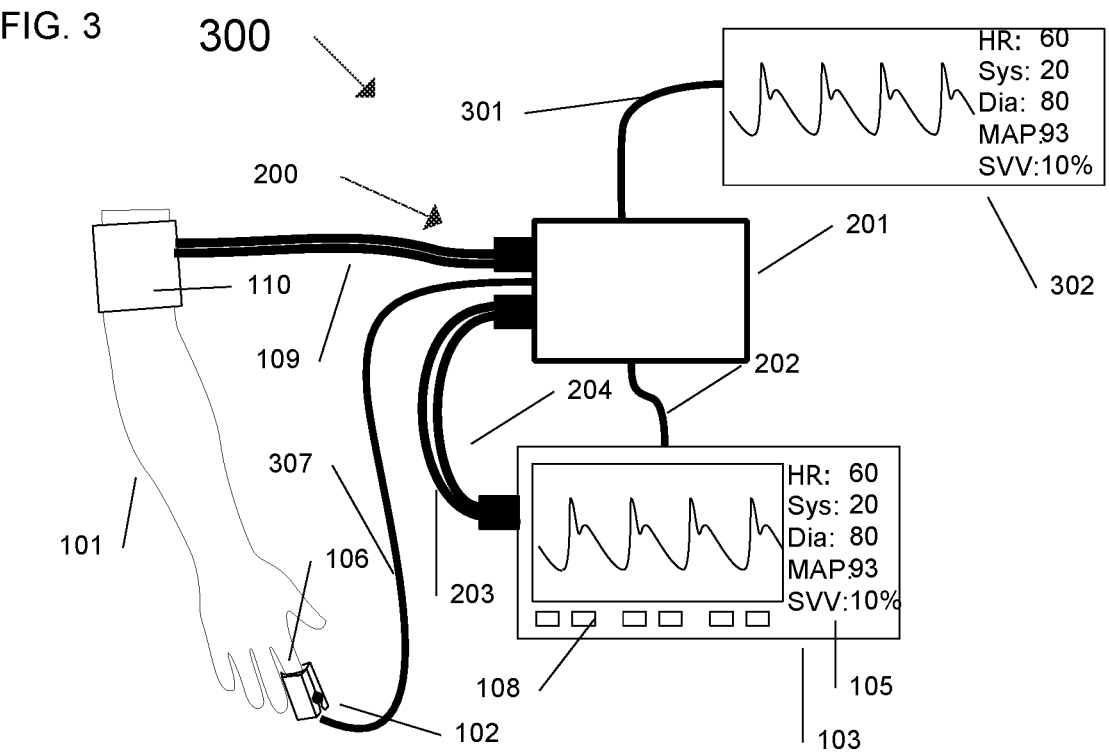
FIG. 3 shows system 300, which is a third embodiment of the invention, and an interrelationship of system 300 with a limb of a subject.

FIG. 3 shows physical components of a system 300 and arm 101 of the subject. System 300 comprises hardware assembly 201, PCM 103, and external display 302.

FIG. 3 shows connection 301 of an external display 302 to hardware assembly 201. External display 302 may be capable of displaying BPV data from hardware assembly 201. Tracking transducer 102 may be connected to hardware assembly 201, to PCM 103, or to both.

Figure 4:
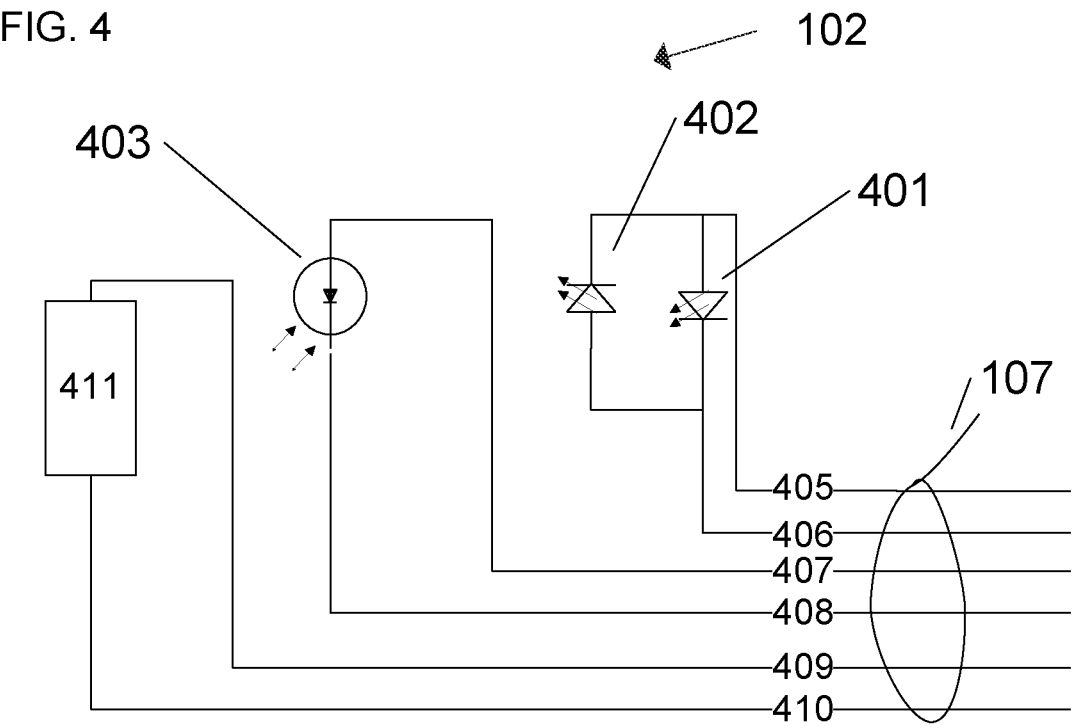
FIG. 4 is a schematic of electrical components of tracking transducer 102.

FIG. 4 is a schematic of electrical components of tracking transducer 102, including light emitting diodes 401 and 402; photodetector PIN diode 403, wires 405 to 410, within cable 107, and authentication device 411. This kind of tracking transducer comprises a combination of one or more light emitting devices and one or more light sensitive devices that when mounted on a subject organ, can detect changes in light absorption in a part of that organ. Transducer 102 comprises a light source and a detector capable of distinguishing a pulsatile component corresponding to arterial pressure. The DC component of the signal is attributable to the bulk absorption of the skin tissue, while the AC component is directly attributable to variation in blood volume the body organ on which it is placed, caused by the pressure corresponding to the cardiac cycle. Typically two light sources are light emitting diodes 401 and 402. LED 401 emits infrared light with wavelength of 940 nm, and LED 402 emits red light, with wavelength of 660 nm. These wavelengths are typical value, and other wavelengths can be used in the infrared and visible regions, including greed light which is also sometimes used. The transducer also includes a photodetector PIN diode 403. The tracking transducer optionally also includes an authentication device 411 which provides the transducer with a unique ID. This arrangement, together with appropriate provision in assembly 201, will safeguard the subject from being fit with a transducer that was used on another subject beforehand. Optional authentication device 411 comprises an integrated circuit ROM programmed with a unique ID and having a single contact one wire interface, like DS28E05 by Maxim Semiconductors.

Tracking transducer 102 connects via cable 107 to a suitable interface. Cable 107 typically comprises 4 or 6 wires. One pair of wires (405,406) for the light sources, one pair (407,408) for the photodetector and optionally a pair (409,410) for the authentication device.

Figure 5:
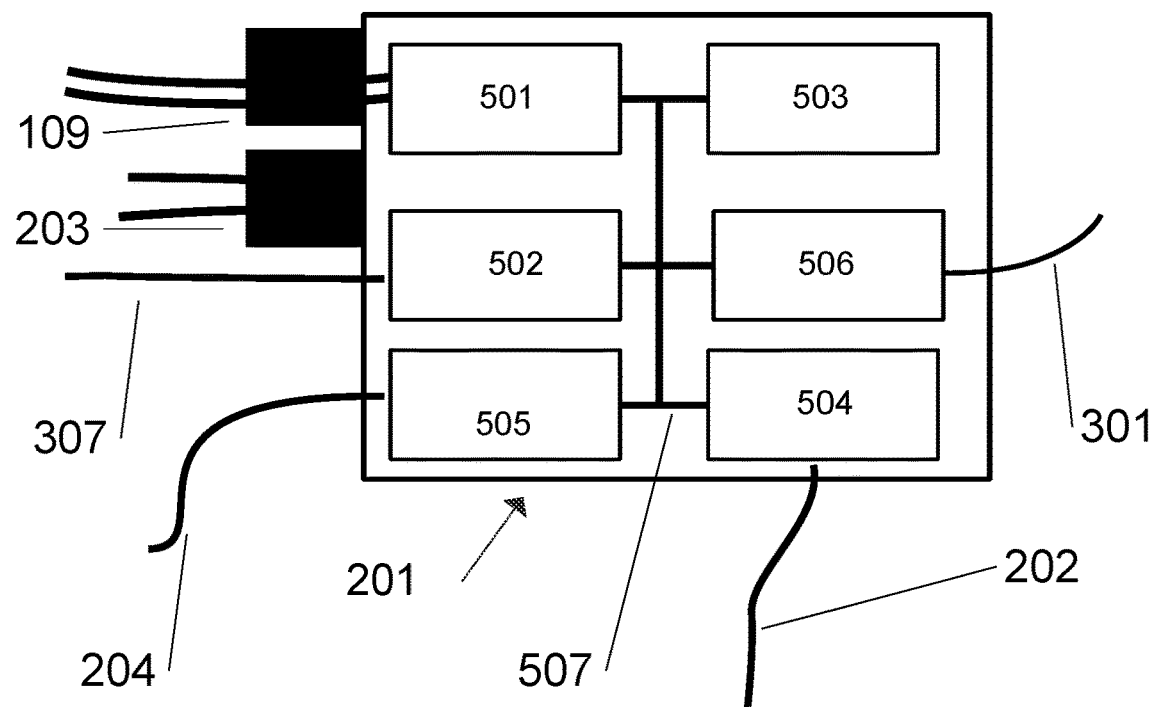
FIG. 5 shows a detailed description of hardware assembly 201 of FIGS. 2 and 3.

FIG. 5 shows hardware assembly 201 including pressure sensor 501; tracking transducer front end 502; processing system 503; digital to analog (D/A) converter 505; interface to PCM 504; and display interface 506. All these circuit blocks are interconnected via digital bus 507.

Circuit blocks: pressure sensor 501; tracking transducer front end 502; display interface 506; and D/A converter 505 are optional. Pressure sensor 501 senses the air pressure provided in cuff 110. PPG front end 502 interfaces to the tracking transducer 102 and provides and interface to the processing system 503. Processing system 503 may run real-time BPV and/or SVV estimation algorithms. Processing system 503 may communicate BPV and/or SVV data to one or more of interface circuit 504; D/A converter 505; and display interface 506.

In embodiments, interface circuit 504 reads the calibration data provided by the PCM 103 and optionally also the data sent by the tracking transducer 102 to the PCM 103. In embodiments, the tracking transducer interfaces to assembly 201 directly, and interface to PCM 504 interfaces to PCM 103 for reading the calibration data. In embodiments, interface to PCM 504 sends the estimated pressure values to PCM 103. In one embodiment, this data is sent to PCM 103 in analog form using D/A converter 505. In embodiments, interface circuit 504 converts BPV and/or SVV data to a form compatible with PCM 103, and transmits the formally compatible data via wire 202 to PCM 103. Interface circuit 304 may format data for transmission serial RS232 connection, USB, Ethernet (LAN), or any other data format in which PCM 103 is capable of receiving BPV and SVV data.

In case of bidirectional communication between hardware assembly 201 and PCM 103, interface 504 may also send data to PCM 103. Interface 504 may send to PCM 103 any one or more of data derived from the calibration sensor (cuff 110) and tracking transducer 102 for display on PCM 103. PCM Designs of interfaces to convert data to desired output data formats, such as the data formats required by any particular PCM model, are well known. The particular data format required for any particular PCM may be proprietary to any particular PCM manufacturer. However, given that proprietary format, programming or designing of an interface, such interface 504, is well within the ability of anyone skilled in the art and a matter of routine engineering and programming.

Figure 6:
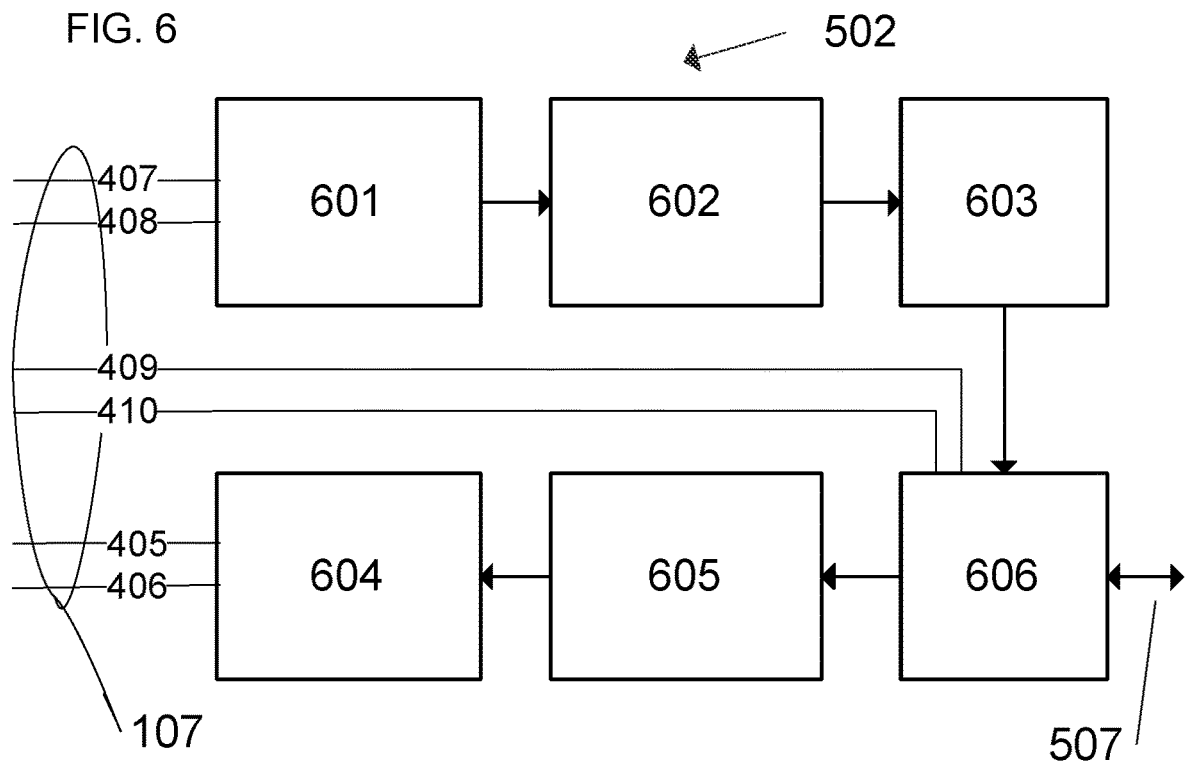
FIG. 6 shows a detailed description of tracking transducer front end 502
Figure 7:
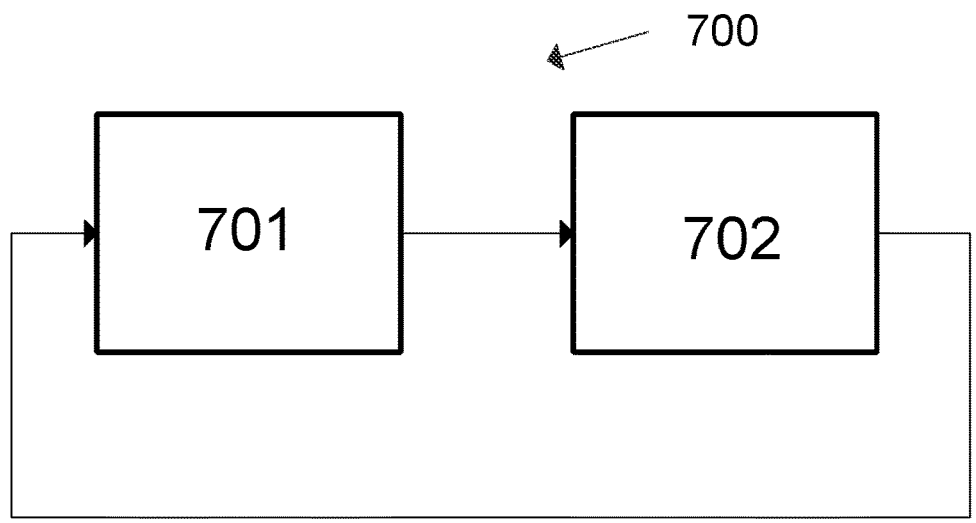
FIG. 7 is a flowchart showing algorithm 700 comprising repetitive calibrate and track activities.

FIG. 6 shows a tracking transducer interface circuit 502. When the tracking transducer is connected with the tracking transducer interface, together they provide the functionality of a photoplethysmographic sensor, which is typically used to monitor the perfusion of blood in the subject tissue.

Tracking transducer interface circuit 502 comprises transimpedance amplifier 601; filter circuit 602; analog to digital (A/D) converter 603; LED driver 604; current control D/A converter 605; and Digital interface circuit 606.

LED driver 604 drives current pulses to the LED's. The current of these pulses is controlled by a current control DAC 605, which in turn is controlled by digital interface circuit 606. The signal from the photodetector 403 is amplified by a transimpedance amplifier 601, is filtered by filter circuit 602 and is sampled by A/D digital converter 603. The signal from 603 is connected to digital interface circuit 606. Digital interface circuit 606 connects to the processor via bus 507. In the case where cable 107 contains a branch that has one side from the branch connecting to hardware assembly 201 and the other side from the branch connecting to PCM 103, LED driver 604 and current control D/A converter 605 are not needed and may not be implemented.

Combined Electrical Model

Figure 8:
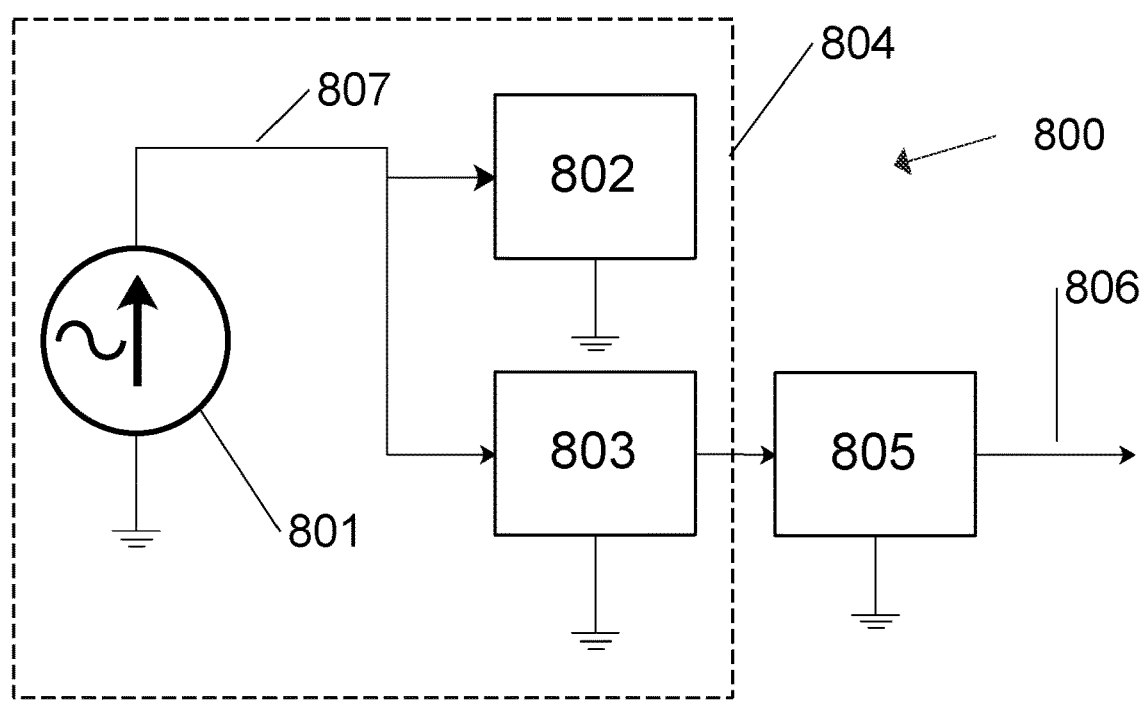
FIG. 8 shows an electrical schematic of a combined electrical model 800 including an electrical model (corresponding to a cardiovascular model) 804 and a model of a tracking sensor 805.

FIG. 8 shows a combined electrical model 800, comprising cardiovascular system electrical model 804 and sensor system model 805.

Cardiovascular system electrical model 804 comprises current source 801; load 802; two-port network 803; equipotential potential connection 807 between output of current source 801 and both input of load 802 and two-port network 803.

Sensor system model 805 defines another two-port network. Sensor system model 805 has an input having an equipotential with an output of two-port network 803. All reference terminals of elements 801; 802; 803; and 805 are referenced to a common ground.

Output 806 of sensor system model 805 is the output of combined electrical model 800.

The frequency domain output signal of the combined electrical model 800 is defined by:

$$Y(w)=N*Xh(w)*Zl(w,\text{MAP})*Hx(w)*Hs(w), \text{ where:} \tag{28}$$

w represents frequency;

N is a real number;

Xh(w) represents the current produced by current source 801.

Zl(w, MAP) represents the input impedance of load 802.

Hx(w) represents the transfer function of two-port 803, having an infinite input impedance.

Hs(w) represents the transfer function of two-port 805.

Xh models pumping of the heart. Zl models impedance of major arteries; Hx models transfer of arterial pressure output near the heart to arterial pressure at pressure measurement location; Hs models change from arterial pressure at the measurement location to tracking sensor output signal.

The asterisk (*) represents multiplication; w represents frequency; and MAP is defined above. The model assumes that Zl is the only MAP dependent function.

For MODEL1(w) is the frequency domain output signal of MODEL1:

$$MODEL1(w) = \frac{1}{Xh(0)*Z1(0)*Hx(0)*Hs(0)} * Xh(w)*Z1(w)*Hx(w)*HS(w), \quad (29)$$

where:

MODEL1 represents the output signal from the combined electrical model, as described in the First Normalization and Fitting Method herein above.

For MODEL2(w) is the frequency domain output signal of MODEL2:

$$MODEL2(w) = \frac{1}{|X_h(w1)*Z_1(w1)*H_x(w1)*H_s(w1)|} * X_h(w)*Z_1(w)*H_x(w)* H_s(w), \quad (30)$$

where:

$Xh(w)$ is the heart function 801 of FIG. 8;

w1 is the frequency of the first harmonic of the arterial pulse that is modeled;

$Zl(w)$ is the heart load impedance represented by load 802 in FIG. 8;

$Hx(w)$ is the heart to fingertip transfer function; and $Hs(w)$ is the transfer function of the tracking sensor front end.

One option for $Xh(w)$ is:

$$Xh(w) = \mathcal{F}\left(e^{(\Gamma*t)} * \left(1 + \frac{t}{FT}\right) * t\right) \quad (31)$$

In this equation, $\Gamma$ and FT are the model parameters, and $\mathcal{F}$ represents a Discrete Fourier Transform (DFT).

The inventor has discovered that a fixed value of $\Gamma$ between 3.0 and 9.0, and preferably $\Gamma$ equals 6.154 is sufficient for tracking of BPV.

FT is one of the model parameters.

In embodiments, the heart function is unity: $Xh(w)=1$, representing the Fourier transform of a Dirac delta function.

In embodiments, $Xh(w)$ is a Fourier transform of a triangular wave:

$$Xh(w)=F\{1-\alpha \text{ for } 0<t\leq 1/\alpha, \text{ and } 0 \text{ otherwise}\} \quad (32)$$

$\alpha$ is a model parameter. In embodiments, a value for $\alpha$ is determined during calibration. In embodiments, a value for $\alpha$ is determined during tracking.

Hs is the transfer function of two port network 805 of FIG. 8. Two port network 805 may comprises a low pass filter providing a finite duration output (FIR filter) and a high pass filter whose response does not become zero at any finite time (IIR filter).

Figure 9:
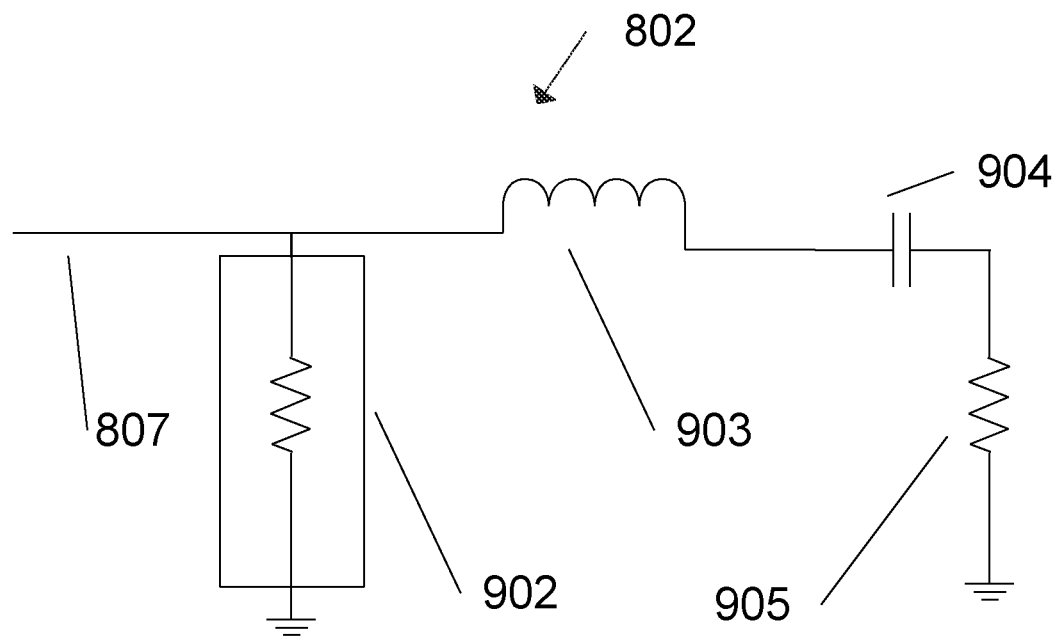
FIG. 9 is an electrical schematic of one embodiment of element 802 in FIG. 8.

FIG. 9 shows an electrical schematic of one embodiment load 802 in FIG. 8.

Load 802 comprises resistor 902, inductor 903, capacitor 904, and resistor 905. Resistors 902, 904 are referenced to common ground and resistor 902 and inductor 903 are connected to equipotential potential connection 807. The value of capacitor 904 correspond to a cardiovascular model in which the capacitance is MAP dependent, and varies as 1/MAP.

For the FIG. 9 schematic:

$$Z_1(w) = \frac{S^2 + \frac{w_0(MAP)}{Q}*S + w_0^2(MAP)}{S^2 + w_0^2(MAP)*\tau*S + w_0^2(MAP)}e^{s*T_s}, \quad (33)$$

where $S=j*w$;

and $w_0$, Q, and $\tau$ are model parameters;

Ts is a parameter representing a time difference between a determined time at which the corresponding cardiac cycle begins and when Systole begins and, and $w_0$, is the zero frequency.

In another embodiment, the $Z_1$ is defined as:

$$Z_1(w) = \frac{S^2 + \frac{w_{01}(MAP)}{Q}*S + w_{01}^2(MAP)}{S^2 + w_{02}^2(MAP)*\tau*S + w_{02}^2(MAP)}e^{s*T_s}, \quad (34)$$

where:

w01, w02, Q, $\tau$, and Ts are model parameters that are determined by fitting.

Figure 10:
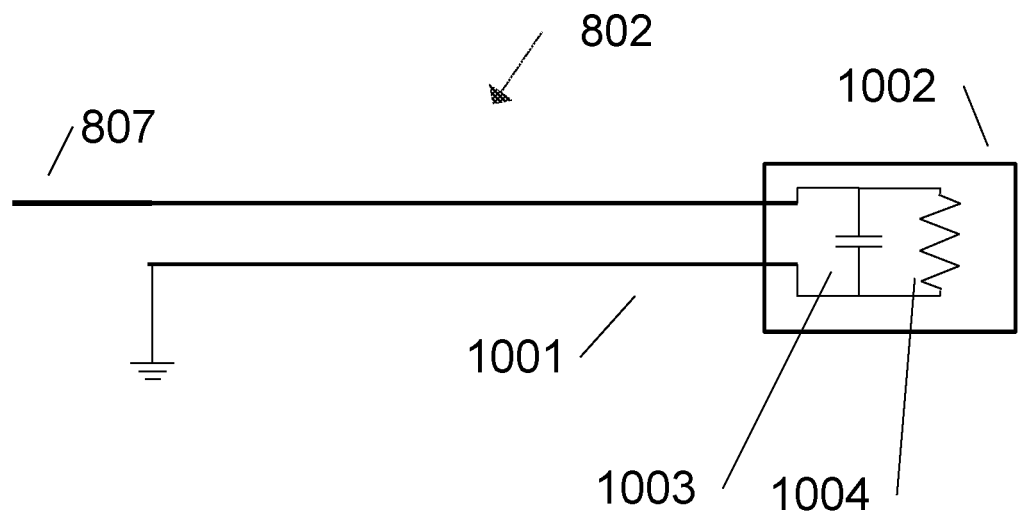
FIG. 10 is an electrical schematic of an alternative embodiment of element 802 in FIG. 8.

FIG. 10 shows an electrical schematic of an alternative embodiment of load 802 in FIG. 8. In FIG. 10, load 802 comprises transmission line 1001 and termination 1002. Termination 1002 comprises capacitor 1003 and resistor 1003 in parallel across the transmission line 1001.

The input impedance to load 802 is:

$$Z1 = Z_0 \frac{Zt + j*Z_0\tan(\beta L)}{Z_0 + j*Zt*\tan(\beta L)} \quad (35)$$

where:

$Z_0$ is a function of MAP;

Zt is the termination impedance defined by the capacitor 1003 and resistor 1003 in parallel across the transmission line 1001;

$\beta$ is a function of w and MAP; and

L is length of transmission line 1001.

In embodiments, $Z_0$ is proportional to sqrt(MAP).

In embodiments, Beta is proportional to w*sqrt(MAP).

In embodiments, the capacitance of capacitor 1003 is proportional to 1/MAP.

Figure 11:
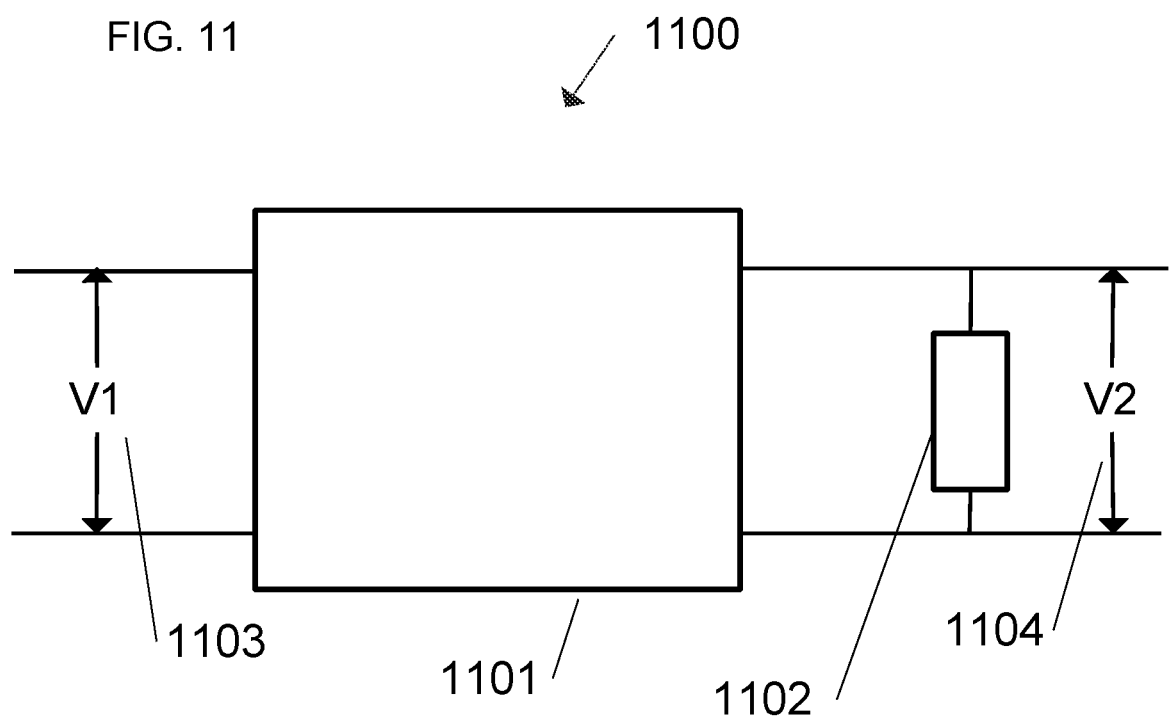
FIG. 11 is a schematic of a two port network 1100 representing one embodiment of two-port network 803, of FIG. 8

FIG. 11 shows a schematic of a two port network 1100 representing one embodiment of two-port network 803, of FIG. 8. Two port network 1100 comprises input 1103 and output 1104, each comprising two terminals, transmission line 1101, and termination 1102. V1 and V2 represent voltages at the input and output respectively.

The transfer function for FIG. 11 is one embodiment of Hx(w). This transfer function is:

$$Hx(w) = \frac{V_2(w)}{V_1(w)} = \frac{1+\Gamma}{e^{j*w*t_d} + \Gamma * e^{-j*w*t_d}}, \quad (36)$$

where:

$t_d$, $\Gamma$, are constants.

Figure 12:
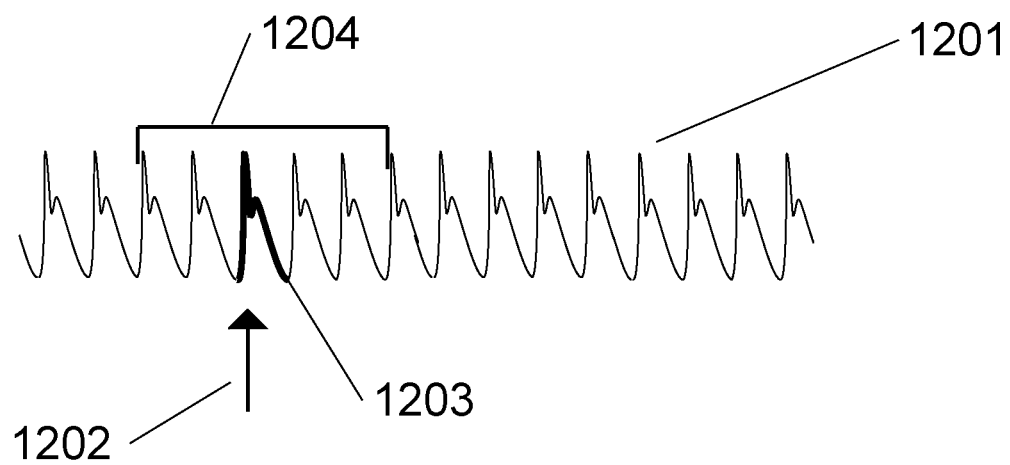
FIG. 12 shows a waveform containing a sequence of arterial pulses, and indicia helpful in explaining a method of calibration.

FIG. 12 shows waveform 1201, time 1202, arterial pulse 1203, and waveform segment 1204 of waveform 1201. FIG. 12 shows waveform segment 1204 spanning a sequence of 5 arterial pulses. All arterial pulses in waveform segment 1204 are relatively close in time, to time 1202. Waveform segment 1204 illustrates a time period over which systems 100, 200, 300 may use tracking data for calibration. The five arterial pulses shown in waveform segment 1204 are for illustrative purposes only. More or fewer arterial pulses from the tracking data may be used, so long as tracking data for at least one arterial pulse is used. Waveform 1201 represents data from the tracking transducer waveform segment 1204 shows a segment containing plural arterial pulses. Waveform 1201 shows semi repetitive arterial pulses which correspond to arterial pressure changes in the location of the subject's body monitored by the tracking sensor, and also correspond to the periods of cardiac cycles. Each arterial pulse shows two maxima separated by a minima corresponding to the dicrotic notch, and with the first maxima higher than the second maxima. Waveform 1201 is for purposes of illustrating the invention and therefore shows relatively identical arterial pulses. Actual arterial pressure waveforms typically have cardiac pulse periods and amplitudes that substantially vary from one another.

Preferably, arterial pulses from the tracking data used for calibration occur within 10 minutes of time 1202, more preferably within 1 minute of time 1202, more preferably within 20 seconds of time 1202, and most preferably within 10 seconds of time 1202 including the arterial pulse overlapping in time with time 1202.

Time 1202 identifies time 1202 that PCM 103 or hardware assembly 201 determined to be the time at which the calibration sensor determined calibration values Ps, Pd, or MAP values. In embodiments, the processing system determines a time at which the calibration sensor obtained data used for determining Ps, Pd, or MAP, and identifies the arterial pulse in the tracking data closest to that time. For example, pulse 1203 spanning time 1202. The processing system uses the data from this pulse 1203 in the calibration process. In other embodiments, the processing system uses the data for pulse 1203 and other pulses, such as the adjacent pulses, in the calibration process, or all pulses in waveform segment 1204.

In one embodiment, arterial pulse 1203 is identified as the one producing the largest pressure fluctuation during one cardiac cycle in the pressure sensor 501 or by PCM 103. During calibration, this arterial pulse frequency content and the calibration values are used to train a model and find the parameters of the model that match the measured signal as closely as possible.

In embodiments which incorporate a cuff of the form used for blood pressure measurement, the processing system may determine the point in time at which the variation of pressure with time is the largest, during one cardiac cycle. The processing system may use tracking sensor data close to this time, as discussed above, for calibration.

Figure 13:
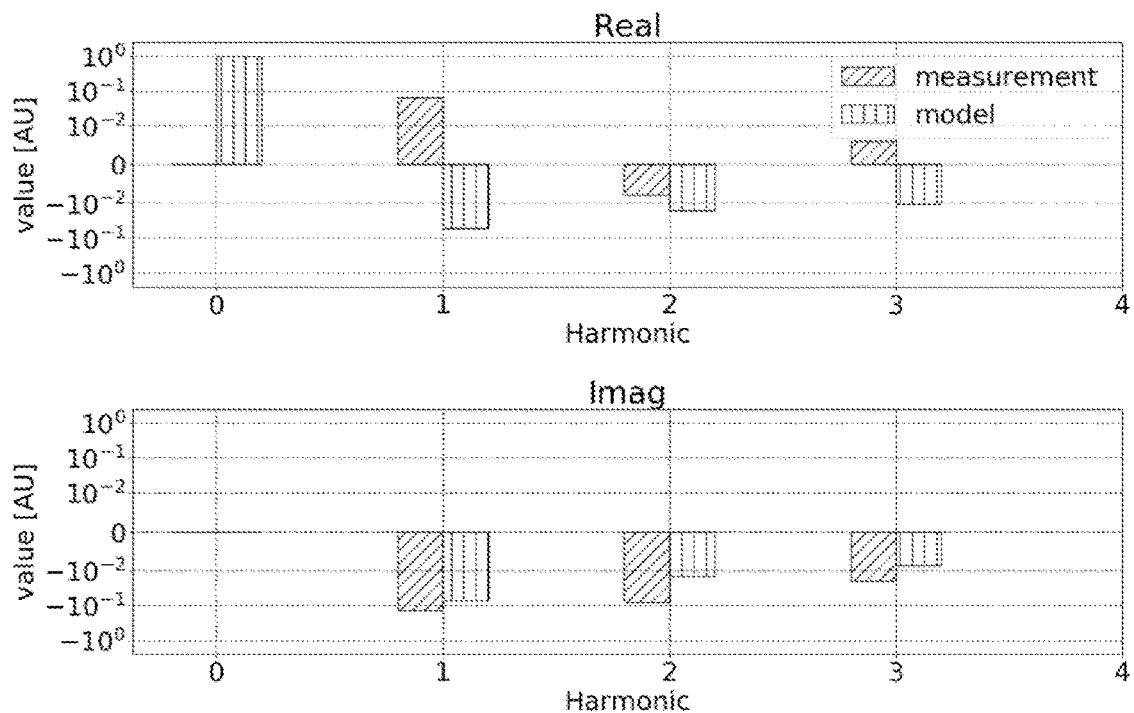
FIG. 13 shows two plots; one for values of real components versus harmonic frequency; and one for values of imaginary components versus harmonic frequency, for both tracking data (measurement) and model data, before fitting.

FIG. 13 shows two plots; one for values of real components versus harmonic frequency; and one for values of imaginary components versus harmonic frequency, for both tracking data (measurement) and model data, before fitting.

FIG. 13's upper plot shows values of real components versus harmonic frequency for tracking data (measurement) and model data. FIG. 13's lower plot shows values of imaginary components versus harmonic frequency for tracking data (measurement) and model data. FIG. 13 shows the data, before fitting the selected model to the tracking data. FIG. 13 shows harmonics along the x axis. The frequencies of these harmonics are integers divided by the cardiac pulse period.

FIG. 13 shows values for the DC component and the harmonic frequencies for values 1, 2, and 3 times the fundamental frequency, for the model.

FIG. 13 shows values for the fundamental frequency and harmonics at 2 and 3 for the tracking data (obtained during one cardiac time period and for the time duration of cardiac time period). FIG. 13 show no DC value for tracking data and DC value of tracking data is not used by the processing system.

Figure 14:
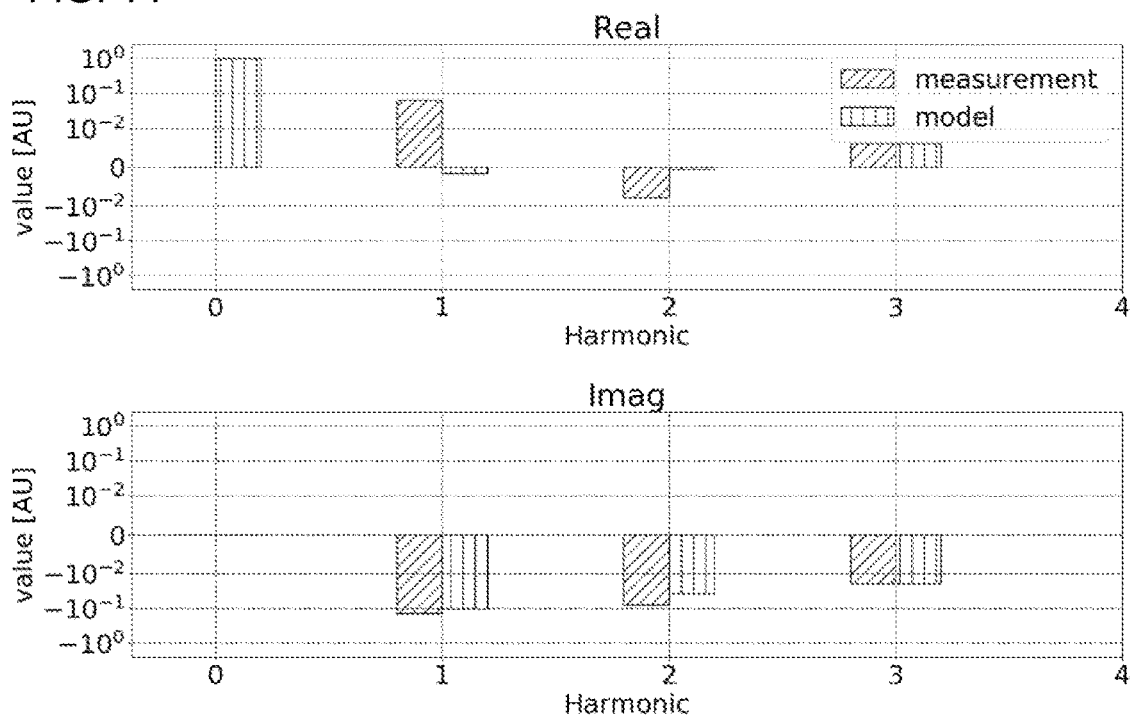
FIG. 14 shows two plots; one for values of real components versus harmonic frequency; and one for values of imaginary components versus harmonic frequency, for both tracking data (measurement) and model data, after fitting.

FIG. 14 shows two plots; one for values of real components versus harmonic frequency; and one for values of imaginary components versus harmonic frequency, for both tracking data (measurement) and model data, after fitting.

FIG. 14 has an upper plot which shows values of real components versus harmonic frequency for tracking data (measurement) and model data. FIG. 14 has a lower plot which shows values of imaginary components versus harmonic frequency for tracking data (measurement) and model data.

FIGS. 13 and 14 show data for the same pulse and therefore for harmonics that have the same frequencies. FIG. 14 shows the data, after fitting. FIG. 14 shows values for the DC component of the model, and values for the harmonics 1, 2, and 3 times the fundamental frequency for both the model and the tracking data. FIG. 14 shows model data that is a best fit to the values of the tracking data harmonics 1, 2, and 3 times the fundamental frequency.

In some embodiments, for fitting for a calibration, $w_0$, Q, $\tau$, F$\tau$ and Ts are allowed to vary to obtain a best fit.

In some embodiments, for tracking, $\tau$ and Ts are fixed, and $w_0$, Q, $\tau$, FT are allowed to vary to obtain a best fit. In this case, $\tau$ and Ts are fixed values that are functions of values for $\tau$ and Ts determined during calibration.

Figure 15:
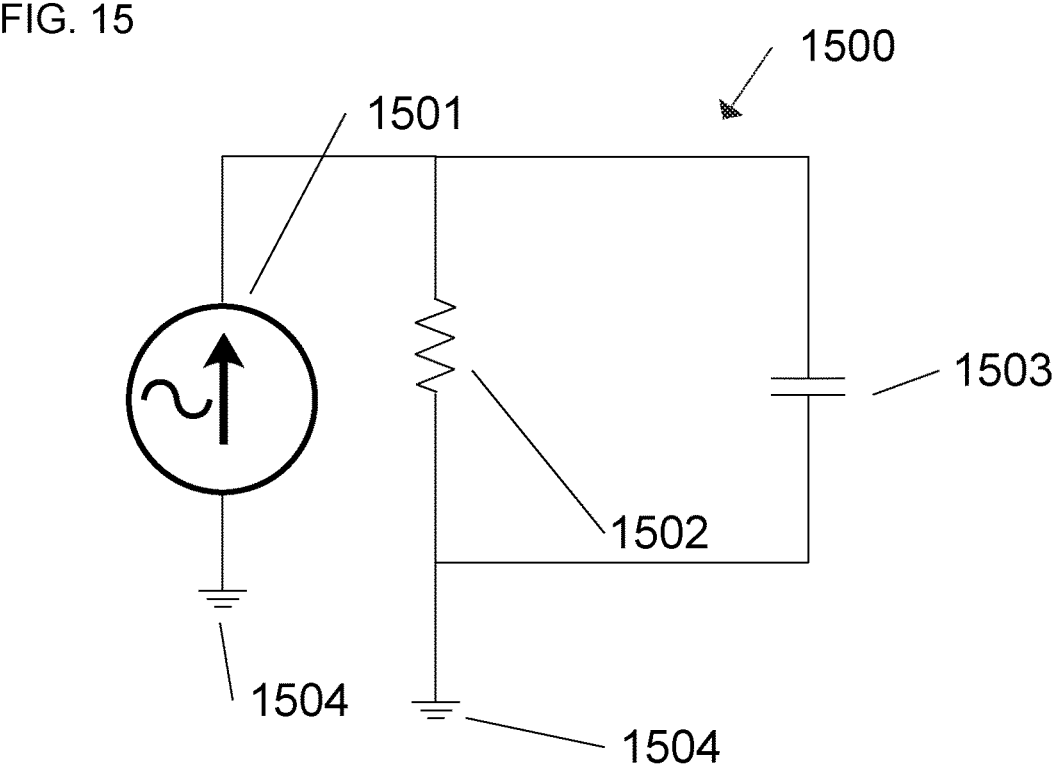
FIG. 15 is an electrical schematic of circuit 1500 corresponding to a cardiovascular model.

FIG. 15 shows an electrical schematic of circuit 1500 corresponding to a cardiovascular model. This model may be used as the basis to determine PP during tracking. FIG. 15 shows electrical circuit 1500 comprising current source 1501, resistor 1502, and capacitor 1503, and grounds 1504. R resistor 1502 and capacitor 1503 are in parallel and referenced to ground 1504. FIG. 15 has a response versus frequency that is a function that has a single pole. At low frequencies up to the fundamental harmonic of the heart, the cardiovascular system can be considered as a single pole system.

Electrical circuit 1500 is a simplified single pole model that may be used by the processing system to determine $\tau_1$ (defined herein below) during calibration. During tracking, the processing system may use $\tau_1$, MAP and PP determined from calibration, and the MAP estimated during tracking, to calculate PP during tracking.

Electrical circuit 1500 has a ratio of the amplitude of the first harmonic, H1, to the DC amplitude, H0, of:

$$\frac{H1}{H0} = \text{abs}\left(\frac{1}{(R*C*S)+1}\right), \quad (37)$$

where:
R is the resistance of resistor 1502;
C is the capacitance of capacitor 1503;
S=j*w where w is angular frequency.

In the corresponding cardiovascular model, C is proportional to 1/MAP. In the corresponding cardiovascular model, PP/MAP=(H1/H0)*K, where K is the number specified in the formula for FSUB. Consequently, this electrical model enables determination of PP for the corresponding cardiovascular model.

MAP and PP values are determined during calibration, to provide MAP1 and PP1. Using these values, $\tau_1$ can be calculated as follows:

$$\tau_1 = \sqrt{\frac{K^2 * \left(\frac{MAP_1}{PP_1}\right)^2 - 1}{w_1^2}}, \quad (38)$$

where
K is the constant defined above $$w1 = \frac{2*\Pi}{IBI_1}; \quad (39)$$

and
$IBI_1$ is the cardiac time period of the other arterial pulse.
PP2 is the estimation of PP for the particular arterial pulse having MAP2.

$$PP2 = PP1 * \frac{MAP2}{MAP1}\sqrt{\frac{(\tau_1*w_1)^2+1}{\left(\tau_1*\frac{MAP_2}{MAP_1}*w_2\right)^2+1}}, \quad (40)$$

where:
MAP 2 is estimated according to the map tacking method above;

$$w2 = \frac{2*\Pi}{IBI_2};$$

and
$IBI_2$ is the cardiac time period of the particular arterial pulse.

In a different embodiment, unrelated to FIG. 15, the processing system may calculate PP2 assuming the following relationship:

$$PP2 = PP1 * \frac{MAP_2}{MAP_1} \quad (41)$$

Figure 16:
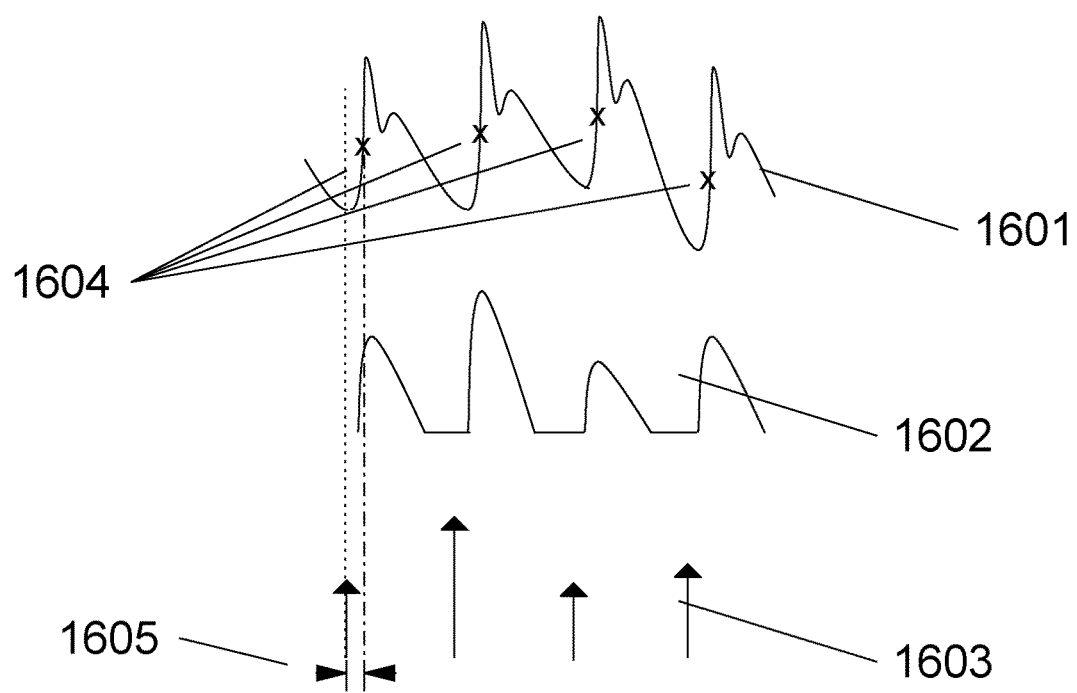
FIG. 16 shows arterial pulse trains and time correspondence to a subject's heart SVs; and delta functions.
Figure 17:
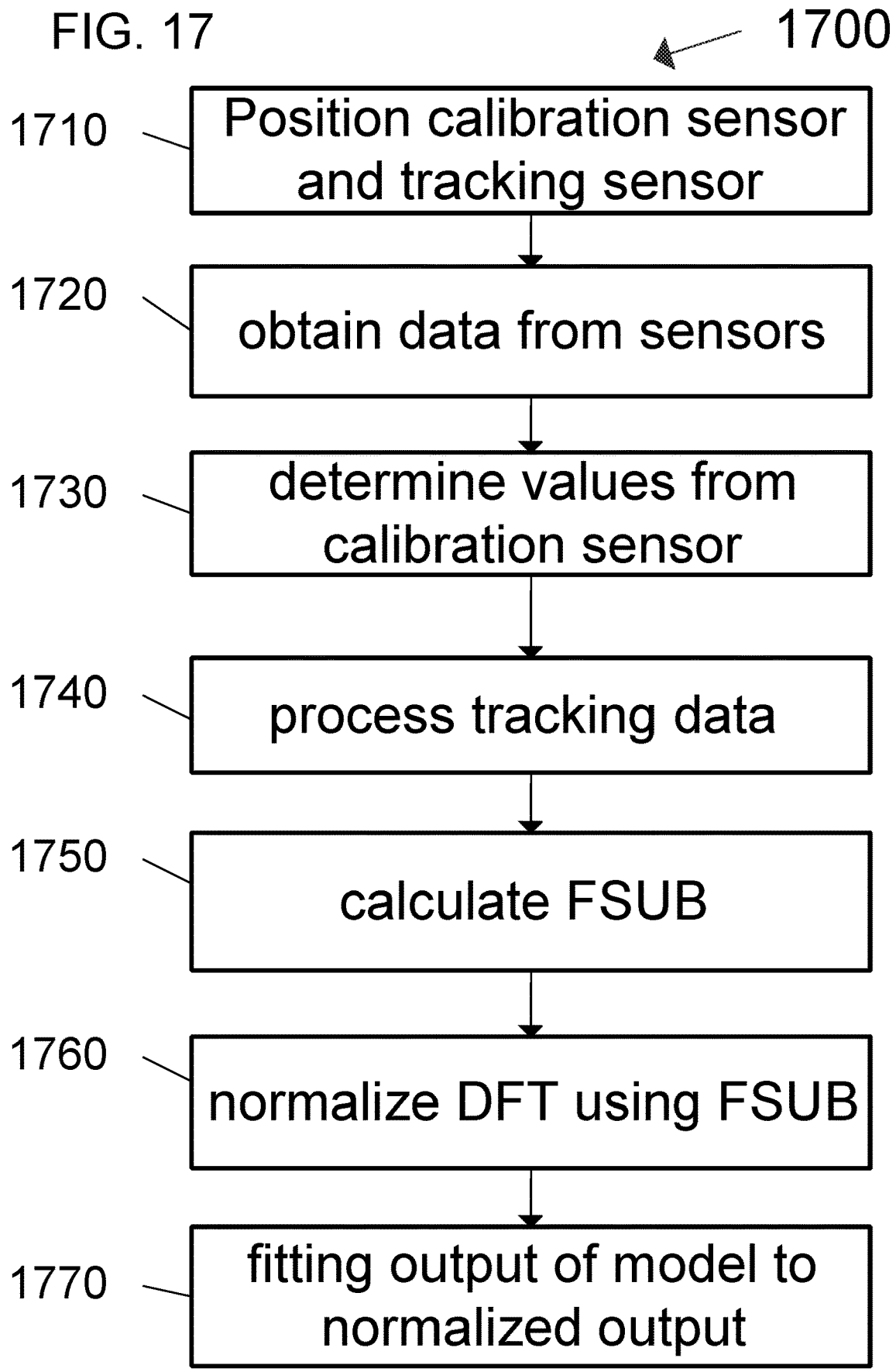
FIG. 17 is a flow chart showing steps of calibration.
Figure 18:
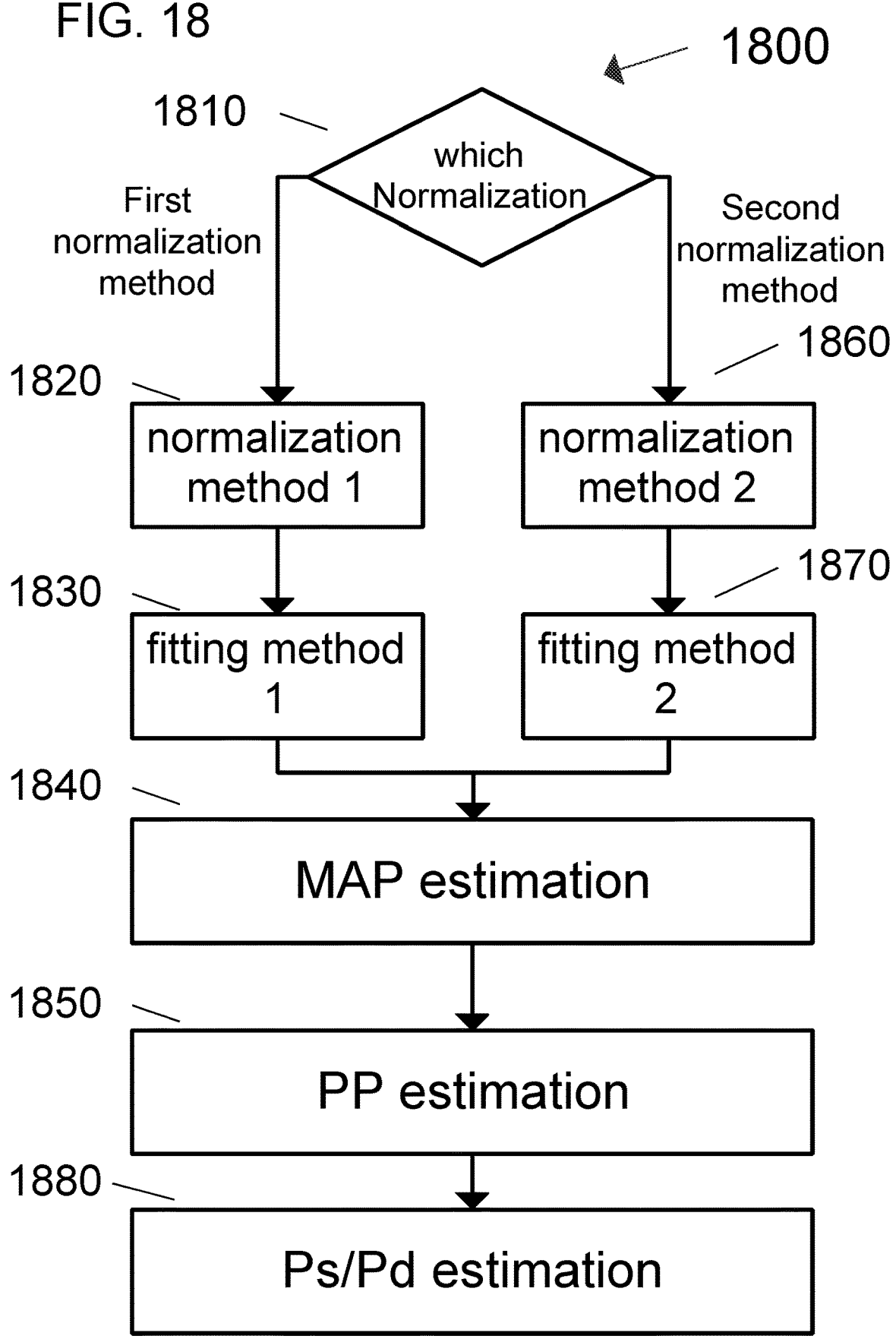
FIG. 18 is a flow chart showing steps of tracking
Figure 19:
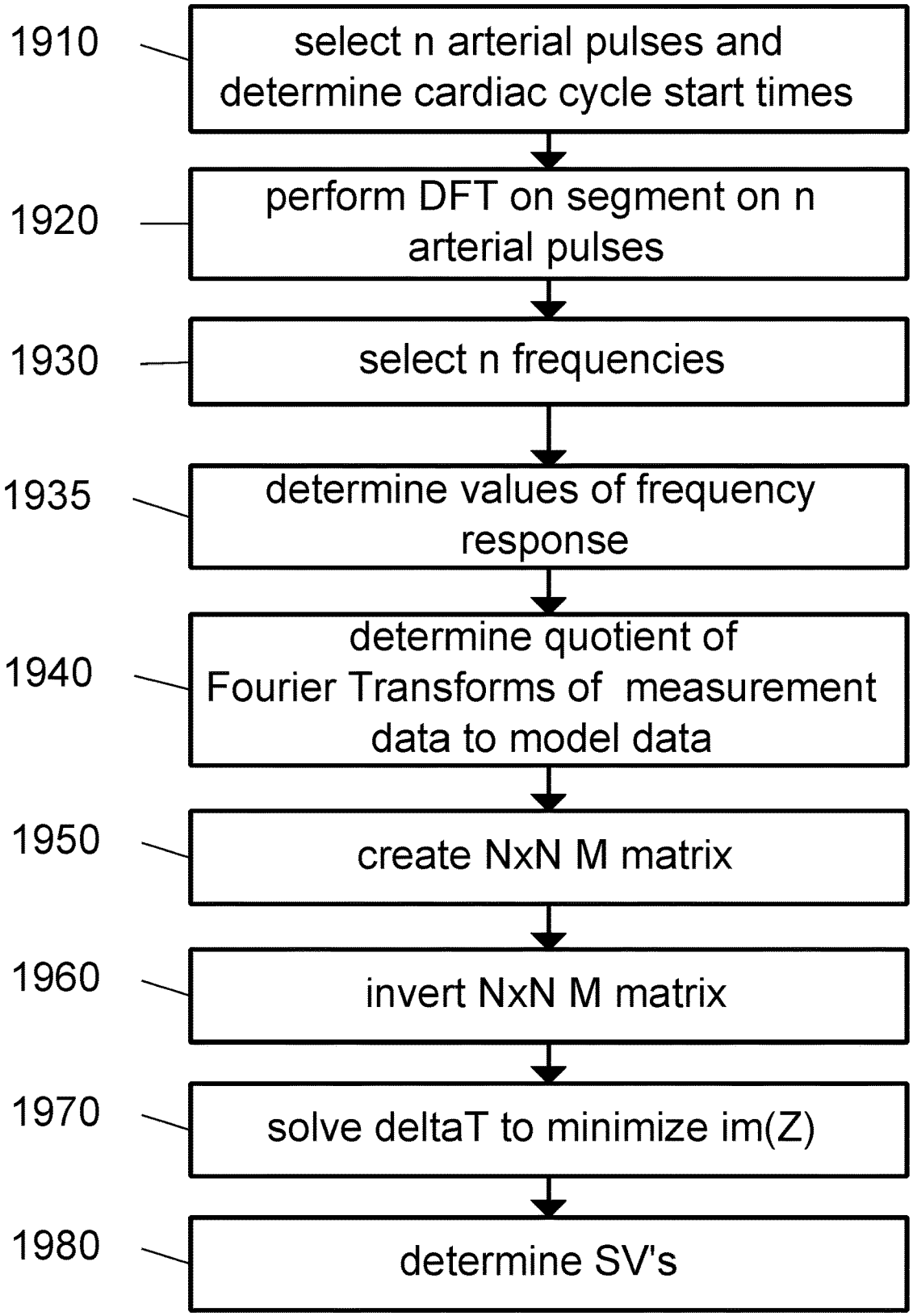
FIG. 19 is a flow chart showing stroke volume estimation.

FIG. 16 shows arterial pulse trains and time correspondence to a subject's heart SVs; and delta functions.

FIG. 16 shows traces 1601, 1602, and delta functions 1603; marker 1604; and time difference deltaT, 1605.

Trace 1601 shows a resultant arterial pressure versus time. Trace 1602 represents heart blood flow versus time. Magnitudes of delta functions 1603 represent values for heart stroke volume at times equal to the end of each diastole phase. Marker 1604 identifies times which the processing system determines from tracking sensor data to be the beginning of cardiac cycles. Marker points 1604 can be identified from the characteristic features as described above in the fourth step of calibration: "PROCESSING TRACKING SENSOR DATA." Time difference 1605 identifies time deltaT between end of diastole and marker point 1604.

Relating Processing to Cardiovascular System

The processing system uses the data shown in FIG. 16 to determine start and end times of cardiac cycles. The processing system uses cardiac cycle start and end times, trace 1601, and a particular cardiovascular model to determine one value for deltaT and the SVs of the cardiac cycles, as described above in the discussion of SV estimation.

The SV estimation process described above is based upon this particular cardiovascular model. This cardiovascular model assumes heart blood flow versus time is a convolution of the series of variable amplitude delta functions, shown by 1603, with a heart function xh(t). For example, xh(t) may be defined by the argument of the Fourier transform of equation (31), which is:

$$xh(t) = e^{(\Gamma*t)} * \left(1 + \frac{t}{FT}\right). \quad (42)$$

The Fourier Transform of the Heart Blood Flow (hbf) versus time is:

$$HBF(w) = \Sigma_{i=0}^{N-1} Xh(w) * SVi * e^{-S*t_i}, \text{ where:} \quad (43)$$

Xh(w) is taken from equation (31);
SVi are the stroke volumes of the i=0, . . . , N−1 stroke volumes, SV.
S=j*w; and
$t_i$ are the instances of impulse i of the delta functions.

The arterial pressure versus time is merely another convolution of the hbf with the impulse response of the corresponding combined electrical model comprising load 802; two-port network 803 and tracking sensor 805 of FIG. 8.

In the frequency domain this can be expressed following equation (29) as:

$$Y(w) = HBF(w) * Hsys(w) \quad (44)$$

Where Hsys(w) is defined as:

$$Hsys(w) = Z1(w)Hx(w)Hs(w) \quad (45)$$

And therefore the equations connecting the stroke volumes to the spectrum of the signal Y(w) as measured by the sensor is:

$$Y(w) = e^{-S*\Delta t} * Hsys(w) \Sigma_{i=0}^{N-1} SV_i * e^{-S*t_i} \quad (46)$$

Both Y(w) and Hsys(ωw) are vectors, that is a series of values, preferable complex, with length equal to the length of the unknown SV, which is also a vector, which is a list of values, preferably real. We can therefore rewrite equation (46) as:

$$\frac{Y(w)}{Hsys(w)} = e^{-S*deltaT}\sum_{i=0}^{N-1} SV_i * e^{-S*t_i} \quad (47)$$

We can equation (47) in matrix notation:

$$[L][M][SV] = \frac{[Y]}{[Hsys]} = [R], \quad (48)$$

where we have defined:

$$[R] = \frac{[Y]}{[Hsys]}, \quad (49)$$

and where M is a matrix of the form $$[M] = \begin{matrix} e^{-j*t_1*w_1} & e^{-j*t_2*w_1} & e^{-j*t_3*w_1} \\ e^{-j*t_1*w_2} & e^{-j*t_2*w_2} & e^{-j*t_3*w_2} \\ e^{-j*t_1*w_3} & e^{-j*t_2*w_3} & e^{-j*t_3*w_3} \end{matrix} \quad (50)$$

L is a diagonal matrix representing the time shift, $$L = \mathrm{diag}(e^{-j*\Delta t*w_1}, e^{-j*\Delta t*w_2}, e^{-j*\Delta t*w_2}, e^{-j*\Delta t*w_3}, \ldots)$$

SV is an array of real SV values, Hsys is as defined in equation (45), and Y(w) is the measured signal at the output.

The system dimension N is the number of arterial pulses in the segment to be analyzed. This is also the number of frequencies at which to perform the analysis.

However, we have N complex equations and N+1 real unknowns. These are the N dimension real vector SV and the real values deltaT.

To solve the system of equations for SV we shall minimize the imaginary part of the SV's by minimizing their sum of squares, by finding the time shift deltaT that minimize the error function:

$$\mathrm{err} = \Sigma_{i=0}^{N-1}(im(SV_i))^2, \quad (51)$$

using a minimization algorithm, for example L-BFGS-B where SV, are result of solving equation (48) for SV.

In one embodiment, the solution for equation (48) is:

$$[SV] = [M]^{-1}[L]^{-1}\frac{[Y]}{[Hsys]} \quad (52)$$

As the frequency domain signal arises from a DFT on an analog signal with an integer number arterial pulses, the N frequencies will be spanned equally, w[n+1]−w[n]=w[n]−w[n−1].

For best quality estimation, the N frequencies to use for solution should be where the signal is strongest, and this occurs around the mean heart rate frequency of the analyzed segment. As N frequencies around this mean frequency are required, it is necessary to include the frequencies F=[HR/2, HR/2+HR/N, HR/2+2*HR/2 . . . 3/2*HR−HR/N] or a small shift of a couple of HR/N from this raster. Practically, the frequency raster is recommended to be between HR/4 to 7/4*HR.

It should be noted, that while the analysis uses a model [Hsys] of the cardiovascular system to solve for the unknown SV, the actual results are insensitive to the exact values of [Hsys]. Therefore, even a sufficient educated guess for the values of this model are sufficient to achieve a good quality estimation of SV.

A system for estimating a ratios of SVs or blood pressure, or both, comprising:

a processing system comprising a processing unit and memory;

the processing system is designed to receive calibration sensor data from a calibration sensor;

the processing system is designed to receive tracking sensor data from a tracking sensor;

the processing system is designed to determine a normalization value based upon a function of the calibration sensor data and the tracking sensor data;

and the processing system is designed to divide at least one harmonic value of the tracking sensor data by the normalization value.

The invention claimed is:

1. A system for estimating values of hemodynamic parameters of a subject, comprising:
    a digital processing system comprising a digital processing unit and digital memory for processing digital data;
    wherein the digital processing system is designed to receive calibration sensor data that relates to arterial pressure from a calibration sensor;
    wherein the digital processing system is designed to receive tracking sensor data from a tracking sensor;
    the digital processing system is designed to calculate estimated hemodynamic values of a hemodynamic parameter based upon:
    one or more outputs, which includes harmonic H2, of a Discrete Fourier Transform (DFT) of tracking sensor data relating to the arterial pressure, and which tracking sensor data was obtained from the subject during a calibration time period;
    at least two of Mean Arterial Pressure (MAP), Pulse Pressure (PP), Systolic pressure (Ps), and Diastolic pressure (Pd) values from data obtained from the subject during the calibration time period;
    one or more outputs of a Discrete Fourier Transform (DFT) of tracking sensor data relating to the arterial pressure, which tracking sensor data was obtained during a tracking time period;
    wherein the tracking time period is different from the calibration time period;
    wherein the digital processing system is designed to display, store or transmit the estimated hemodynamic values; and
    wherein the digital processing system is designed to determine parameters of a fitting function by fitting the fitting function to the DFT of tracking sensor data relating to the arterial pressure obtained from the subject during the calibration time period.

2. The system of claim 1:
    wherein the digital processing system is designed to calculate a value of a function of variables comprising: MAP; PP; and a value of a harmonic of a DFT of tracking sensor data obtained from the subject; and the function is referred to herein as the FSUB function and the value of the function so calculated is referred to herein as an FSUB value.

3. The system of claim 1, wherein a parameter of the fitting function depends upon MAP.

4. The system of claim 1,
wherein the digital processing system is designed to determine parameters of a fitting function by fitting the fitting function to the DFT of tracking sensor data relating to the arterial pressure obtained from the subject during the tracking time period.

5. The system of claim 1, wherein the digital processing system is designed to hold constant the value of at least one determined parameter that was determined from data obtained from the subject during the calibration time period, when fitting tracking data during the tracking time period.

6. The system of claim 1:
wherein the digital processing system is designed to calculate a value for MAP that relates to blood pressure of the subject during the tracking time period, from data comprising values for parameters calculated during the calibration time period, and tracking sensor data obtained from the subject during the tracking time period.

7. A system for estimating values of hemodynamic parameters of a subject, comprising:
a digital processing system comprising a digital processing unit and digital memory for processing digital data;
wherein the digital processing system is designed to receive calibration sensor data that relates to arterial pressure from a calibration sensor;
wherein the digital processing system is designed to receive tracking sensor data from a tracking sensor;
the digital processing system is designed to calculate estimated hemodynamic values of a hemodynamic parameter based upon:
one or more outputs of a Discrete Fourier Transform (DFT) of tracking sensor data relating to the arterial pressure, and which tracking sensor data was obtained from the subject during a calibration time period;
at least two of Mean Arterial Pressure (MAP), Pulse Pressure (PP), Systolic pressure (Ps), and Diastolic pressure (Pd) values from data obtained from the subject during the calibration time period;
one or more outputs of a Discrete Fourier Transform (DFT) of tracking sensor data relating to the arterial pressure, which tracking sensor data was obtained during a tracking time period;
wherein the tracking time period is different from the calibration time period;
wherein the digital processing system is designed to display, store or transmit the estimated hemodynamic values;
wherein the digital processing system is designed to calculate a value for MAP that relates to blood pressure of the subject during the tracking time period, from data comprising values for parameters calculated during the calibration time period, and tracking sensor data obtained from the subject during the tracking time period;
wherein the digital processing system is designed to calculate a value for MAP that relates to blood pressure of the subject during the tracking time period, from data also comprising the value for MAP obtained from the subject during the calibration time period.

8. A system for estimating values of hemodynamic parameters of a subject, comprising:
a digital processing system comprising a digital processing unit and digital memory for processing digital data;
wherein the digital processing system is designed to receive calibration sensor data that relates to arterial pressure from a calibration sensor;
wherein the digital processing system is designed to receive tracking sensor data from a tracking sensor;
the digital processing system is designed to calculate estimated hemodynamic values of a hemodynamic parameter based upon:
one or more outputs of a Discrete Fourier Transform (DFT) of tracking sensor data relating to the arterial pressure, and which tracking sensor data was obtained from the subject during a calibration time period;
at least two of Mean Arterial Pressure (MAP), Pulse Pressure (PP), Systolic pressure (Ps), and Diastolic pressure (Pd) values from data obtained from the subject during the calibration time period;
one or more outputs of a Discrete Fourier Transform (DFT) of tracking sensor data relating to the arterial pressure, which tracking sensor data was obtained during a tracking time period;
wherein the tracking time period is different from the calibration time period;
wherein the digital processing system is designed to display, store or transmit the estimated hemodynamic values;
wherein the digital processing system is designed to determine parameters of a fitting function by fitting the fitting function to another function of output of a DFT of tracking sensor data, for data obtained from the subject during the calibration time period;
wherein:
the digital processing system is designed to determine a value for MAP by computations comprising computing the function $$MAPest = MAPcalib*P(w0est)/Q(w0est)*Q(w0calib)/P(w0calib),\ where:$$

P represents a polynomial;
Q represents a polynomial;
w0est is a model parameter;
w0Calib is a model parameter; and
MAPcalib is a value for MAP obtained during a calibration time period.

9. The system of claim 7 wherein:
the digital processing system is designed to calculate a value for MAP by computations comprising computing the function $MAPest = MAPcalib*w0est2/w0calib2$, where:
w0est is a model parameter;
w0calib is a model parameter; and
MAPcalib is a value for MAP obtained during a calibration time period.

10. The system of claim 4:
wherein the digital processing system is designed to calculate a PP tracking value for PP from values for parameters determined during the calibration fitting and the tracking fitting, and the value for PP obtained during that calibration time period.

11. The system of claim 4:
wherein the digital processing system is designed to determine a PP tracking value for PP from values for parameters determined during the calibration fitting and the tracking fitting, the value for PP obtained during that calibration time period, and the value of at least one arterial time period during the calibration time period and the value of at least one arterial time period during the tracking time period.

12. The system of claim 1 further comprising:
a calibration sensor;
a tracking sensor; and
a device for visually displaying or transmitting values for hemodynamic parameters.

13. The system of claim 2:
wherein the digital processing system is designed to compute values from (1) values of a DFT of tracking sensor data and (2) the FSUB value of the FSUB function.

14. A system for estimating values of hemodynamic parameters of a subject, comprising:
a digital processing system comprising a digital processing unit and digital memory for processing digital data;
wherein the digital processing system is designed to receive calibration sensor data that relates to arterial pressure from a calibration sensor;
wherein the digital processing system is designed to receive tracking sensor data from a tracking sensor;
the digital processing system is designed to calculate estimated hemodynamic values of a hemodynamic parameter based upon:
one or more outputs of a Discrete Fourier Transform (DFT) of tracking sensor data relating to the arterial pressure, and which tracking sensor data was obtained from the subject during a calibration time period;
at least two of Mean Arterial Pressure (MAP), Pulse Pressure (PP), Systolic pressure (Ps), and Diastolic pressure (Pd) values from data obtained from the subject during the calibration time period;
one or more outputs of a Discrete Fourier Transform (DFT) of tracking sensor data relating to the arterial pressure, which tracking sensor data was obtained during a tracking time period;
wherein the tracking time period is different from the calibration time period;
wherein the digital processing system is designed to display, store or transmit the estimated hemodynamic values;
wherein the digital processing system is designed to determine parameters of a fitting function by fitting the fitting function to another function of output of a DFT of tracking sensor data, for data obtained from the subject during the calibration time period;
wherein:
said digital processing system stores a combined electrical model that corresponds to a cardiovascular model and a model of a tracking sensor coupled to arterial pressure at a location in the subject;
wherein said combined electrical model comprises a current source; a load; and
at least one two-port network; and an equipotential potential connection between output of said current source and input of both said load and said at least one two-port network.

15. The system of claim 14:
wherein said combined electrical model comprises a second two-port network that has an equipotential connection to an output of said least one two-port network.

16. The system of claim 1 wherein said digital processing system stores an electrical model that comprises a series connection of an inductor and capacitor, and capacitance of said capacitor is proportional to 1/MAP.

17. The system of claim 1 wherein said digital processing system stores an electrical model that comprises a transmission line, and a parameter of said transmission line is a function of MAP.

18. A method for estimating values of hemodynamic parameters of a subject, using a system comprising a digital processing system comprising a processing unit and memory, and comprising:
receiving calibration sensor data that relates to arterial pressure from a calibration sensor in the digital processing system;
receiving tracking sensor data from a tracking sensor, in the digital processing system;
the digital processing system calculating estimated hemodynamic values of a hemodynamic parameter based upon:
one or more outputs, which includes harmonic H2, of a Discrete Fourier Transform (DFT) of tracking sensor data relating to the arterial pressure, and which tracking sensor data was obtained from the subject during a calibration time period;
at least two of Mean Arterial Pressure (MAP), Pulse Pressure (PP), Systolic pressure (Ps), and Diastolic pressure (Pd) values from data obtained from the subject during the calibration time period;
one or more outputs of a Discrete Fourier Transform (DFT) of tracking sensor data relating to the arterial pressure, which tracking sensor data was obtained during a tracking time period; and
wherein the tracking time period is different from the calibration time period;
wherein the digital processing system is designed to display, store or transmit the estimated hemodynamic values; and
the digital processing system determining parameters of a fitting function by fitting the fitting function to the DFT of tracking sensor data relating to the arterial pressure obtained from the subject during the calibration time period.

* * * * *